US008628953B2

(12) United States Patent
Osato et al.

(10) Patent No.: US 8,628,953 B2
(45) Date of Patent: Jan. 14, 2014

(54) CAPTURING CARRIER, CAPTURING DEVICE, ANALYSIS SYSTEM USING THE SAME, AND METHOD FOR CAPTURING AND TESTING MICROORGANISMS

(75) Inventors: Noe Osato, Toshima (JP); Ryusuke Gotoda, Toshima (JP); Satoshi Ozawa, Mitaka (JP); Hideyuki Noda, Kokubunji (JP); Masahiro Okanojo, Kokubunji (JP)

(73) Assignee: Hitachi Plant Technologies, Ltd., Tokyo (JP)

( * ) Notice: Subject to any disclaimer, the term of this patent is extended or adjusted under 35 U.S.C. 154(b) by 733 days.

(21) Appl. No.: 12/292,626

(22) Filed: Nov. 21, 2008

(65) Prior Publication Data

US 2009/0142785 A1 Jun. 4, 2009

(30) Foreign Application Priority Data

Nov. 29, 2007 (JP) ................................ 2007-309342
Dec. 4, 2007 (JP) ................................ 2007-313066

(51) Int. Cl.
*C12M 1/00* (2006.01)

(52) U.S. Cl.
USPC .................................. 435/289.1; 435/287.9

(58) Field of Classification Search
USPC .......................................... 435/287.9, 289.1
See application file for complete search history.

(56) References Cited

U.S. PATENT DOCUMENTS

| 4,396,716 A * | 8/1983 | Marconi et al. ............... 435/181 |
| 4,464,468 A * | 8/1984 | Avrameas et al. ............ 435/177 |
| 6,228,574 B1 | 5/2001 | Rotman |
| 6,406,906 B1 | 6/2002 | Herbig et al. |
| 6,562,583 B1 | 5/2003 | Herbig et al. |
| RE39,347 E * | 10/2006 | Ikemoto ......................... 428/213 |
| 2004/0002126 A1 | 1/2004 | Houde et al. |

FOREIGN PATENT DOCUMENTS

| EP | 0 781 851 A2 | 7/1997 |
| EP | 0 789 778 81 | 5/2001 |
| EP | 1 504 812 A1 | 2/2005 |
| JP | A-2001-511356 | 8/2001 |
| JP | A-2002-510501 | 4/2002 |
| JP | A-2002-330740 | 11/2002 |
| JP | A-2004-2229 | 1/2004 |
| JP | A-2005-516213 | 6/2005 |
| JP | A-2005-253365 | 9/2005 |
| JP | A-2006-174751 | 7/2006 |
| JP | A-2007-159520 | 6/2007 |
| WO | WO 95/25811 A1 | 9/1995 |
| WO | WO 99/05310 | 2/1999 |
| WO | WO 99/51765 A1 | 10/1999 |
| WO | WO 03/065009 A2 | 8/2003 |
| WO | WO 2004/053051 A2 | 6/2004 |

OTHER PUBLICATIONS

Jeong et al. "Thermoreversible gelation of PEG-PLGA-PEG triblock copolymer aqueous solutions", Macromolecules, 1999, 32:7064-7069.*
Arai et al. "Isolation and extraction of target microbes using thermal sol-gel transformation", Analyst, 2003, 128:547-551.*
Ichikawa et al. "In situ formation of a gel microbead for indirect laser micromanipulation of microorganisms", Applied Physics Letters, 2005, 87:191108-1-191108-3.*
Miyawaki et al. "Effect of water potential on sol-gel transition and intermolecular interaction of gelatin near the transition temperature", Biopolymers, 2003, 70:482-491.*
Hosokawa et al., Eds. "Nanoparticle technology handbook; Application 27", 2007, pp. 531-538.*
Singh "Exocellular proteases of *Malbranchea gypsea* and their role in keratin deterioration", Mycopathologia, 1999, 143:147-150.*
Yoshimura et al. "Physical properties of shark gelatin compared with pig gelatin", J. Agric. Food Chem 2000, 48:2023-2027.*
Jeong et al. "Thermosensitive sol-gel reversible hydrogels", Advanced Drug Delivery Reviews, 2002, 54:37-51.*
Dec. 28, 2012 Office Action issued in Japanese Application No. JP2007-309342 (with English Translation).
Jun. 13, 2012 Notification of Reason(s) for Refusal issued in Japanese Application No. 2007-309342 with English-language translation.
Aug. 6, 2012 Search Report cited in Application No. 201005537.4.
Aug. 6, 2012 Search Report cited in Application No. 201005538-2.

* cited by examiner

*Primary Examiner* — Bin Shen
(74) *Attorney, Agent, or Firm* — Oliff & Berridge, PLC

(57) ABSTRACT

In order to make a process of capturing and testing air-borne microorganisms more convenient and quick, a capturing device which comprises the capturing carrier comprising a polymer which is in a gel phase at the time of capturing the microorganisms but undergoes a phase transition under heating to a sol phase at the temperature at or less than 40° C. (especially in the temperature range between 15° C. and 37° C.), and a vessel to contain the capturing carrier is used. Further, by comprising a test reagent in the polymer, the test reagent can be eluted upon said phase transition from a gel phase to a sol phase. By heating the capturing carrier, a phase transition to a sol phase can occur at or less than 40° C. As such, since recovery of microorganisms and addition of a test reagent to the microorganisms can be carried out simultaneously, the process can be simplified and the process time can be shortened.

25 Claims, 11 Drawing Sheets

Fig.4

Luminescence output of a model capturing carrier with different composition of the ATP eliminating agent

| Content ratio of the ATP eliminating agent [%] | Luminescence output [cps] |
|---|---|
| 0 | 7178 |
| 0.03 | 103 |
| 0.1 | 57 |

Fig.5

Temperature and filtration property of a model capturing carrier with different composition of gelatin

| Gelatin concentration [wt%] | Temperature property | | Filtration property |
|---|---|---|---|
| | 25°C | 37°C | |
| 5 | Soft gel | Transformed into a sol after 4 minutes | Easily passed through |
| 7.5 | Slightly hard | Transformed into a sol after 4 minutes | Passed through after 30 to 40 seconds |
| 10 | Hard gel | Transformed into a sol after 5 minutes | Some could not pass through |

Fig.6

Temperature and filtration property of a model capturing carrier with different composition of glycerol

| Glycerol concentration [wt%] | Temperature property | | Filtration property |
|---|---|---|---|
| | 25°C | 37°C | |
| 30 | Soft gel | Transformed into a sol after 3 minutes | Passed through after 10 seconds |
| 40 | Soft gel | Transformed into a sol after 4 minutes | Passed through after 15 seconds |
| 50 | Slightly hard | Transformed into a sol after 4 minutes | Passed through after 30 to 40 seconds |
| 60 | Hard gel | Transformed into a sol after 5 minutes | Some could not pass through |

Fig.7

Comparison of the recovery property between the first embodiment and the conventional method

| Item | The first embodiment | Conventional method |
|---|---|---|
| ATP amount contained in the sample [amol] | 438, 648 | 126 |
| Average count of the viable microbes in the sample [CFU] | 219, 324 | 64 |
| Recovery ratio | 44%, 65% | 13% |

Fig.10

Comparison of the property of the capturing carrier having
a different synthetic polymer

| Item | Condition | MB−10 | NAGAm/MBPDA |
|---|---|---|---|
| Temperature property | (1) 15°C | Soft gel | Slightly hard gel |
| | (2) 37°C | Hard gel | Sol |
| | (3) 15°C | Sol | Slightly hard gel |
| Filtration property | 4wt% | (Not determined) | Could not pass through |
| | 1.3wt% | | Easily passed through |

CAPTURING CARRIER, CAPTURING DEVICE, ANALYSIS SYSTEM USING THE SAME, AND METHOD FOR CAPTURING AND TESTING MICROORGANISMS

BACKGROUND OF THE INVENTION (a) Field of the Invention

The present invention relates to a capturing carrier for capturing air-borne microorganisms, a capturing device comprising the same, an analysis system using the same, and a method for capturing and testing microorganisms.

(b) Description of the Related Art

As a method for detecting air-borne microorganisms, a colony counting method using an agar medium, or a method for measuring turbidity using a liquid medium and the like have been known. According to these methods, air-borne microorganisms are captured in a medium and cultured for one to several days followed by a test. Accordingly, these methods have disadvantages in that it takes a long period of time for testing, and insuring biologically safety becomes difficult due to cultured microorganisms. As such, their on-line introduction to a production line of food products or pharmaceuticals is impossible. In particular, this type of method for testing microorganisms is often used for determination of microbial cleanness (i.e., germ-freeness) of an environment which requires a high level of cleanness, such as a factory for producing pharmaceuticals, a facility for processing cells, or a factory for producing food. When a culture method is used for on-site test of microorganisms under the environments, if microorganism that are amplified in a massive amount as a product of inspection process are incorporated into the site, a purpose of ensuring the cleanness of the environment cannot be preserved. As a result, there has been a problem that on-site testing cannot be easily carried out. Moreover, installation of a testing room and strict management of a products during production and carrying process are required.

Recently, in order to solve such problems, various methods have been devised by which microbial count is determined quickly and conveniently without culturing them, i.e., without a risk of biological contamination. Specifically, a method has been suggested by which constituents of a microorganism are specifically labeled by using a luminescent or a fluorescent reagent, and then luminescence and luminescence output are measured to determine the microbial biomass. As a first method, there is a method in which microorganisms contained in a sample are stained with two kinds of fluorescent reagents, and then viable and non-viable microbes are counted based on a fluorescence microscopic image analysis and the like (i.e., a fluorescent method). As a second method, ATPs are extracted from the microorganisms contained in a sample, and a biological luminescence reaction by ATP is measured by a luminometer to quantify the ATPs, and it is converted to the viable microbial count (i.e., ATP method).

However, although in principle measurement of one microbial cell is possible according to the first method, co-existence of a fluorescent contaminating material in a sample can cause an error. Further, it is not always easy to differentiate a viable cell from a non-viable cell. For instances, propidium iodide (PI), which is known for selective staining of non-viable cells, may sometimes induce lower average fluorescent intensity for non-viable cells compared to that for viable cells ("Technical Product Information "Live/Dead BacLight™ bacterial viability and counting kit (L34856)" Molecular Probes, edited version of Feb. 2, 2004", FIG. 1C, the vertical axis represents fluorescent intensity of PI), thus there is a high chance of providing an opposite conclusion if careful attention is not paid.

According to the second method, i.e., ATP method, a molecule of ATP (adenosine triphosphate) that is a chemical contained by every living cell is taken as an indicator of the microbial count. This method takes an advantage of a biological luminescence between a luciferase as an enzyme originated from a bioorganism, and luciferin (a kind of imidazopyrazinones) as a substrate for the enzyme. Specifically, after ATPs are extracted from a sample comprising microorganisms, a mixture comprising luciferin and luciferase is added thereto for a luminescence reaction. Then, the amount of ATPs is obtained from the luminescence output, and it is converted to the amount of the microorganisms. As a result, according to this ATP method, the amount of the viable microorganisms can be determined within several minutes to several tens of minutes.

When the amount of the microorganisms is to be determined according to ATP method, an ATP eliminating agent is first added to remove free ATPs that exist outside the cell body of a viable microbe (i.e., extracellular ATPs and ATPs of non-viable microbes) and the resulting free ATPs are decomposed. Then, in order to extract ATPs from the viable cells, an ATP extracting agents is added and cell membrane of the viable microbe is destroyed to elute the ATPs contained inside the cell body of the microbe. Consequently, a luminescent reagent is added and luminescence output is measured, which is then converted to the ATP amount.

Because this ATP method is based on a biological luminescence reaction which selectively responds to ATP, in principle it is not affected by the presence of a fluorescent contaminating material. In addition, a reagent kit, which comprises an ATP eliminating agent which can remove in advance ATPs that exist outside the cell body of a viable microbe, an ATP extracting reagent for extracting ATPs from the viable microbe, and a luminescent reagent for measuring the extracted ATPs based on their biological luminescence reaction, has been commercially provided by Kikkoman Corp. (Product name; Lucifer HS set) (Journal of Japan Society for Bioscience, Biotechnology, and Agrochemistry, Vol. 78, No. 7, p. 630-635 (2004) "Application and development of a firefly luciferase" Murakami Seiji et. al). When this kit is used in conjunction with a luminometer, an influence by non-viable microbes and the like is excluded so that ATP amount solely originating from viable microbes can be selectively measured.

However, the test sample to be tested by the ATP method is a microorganism that is dispersed in an aqueous solution and its application to air-borne microbes has not been suggested. Meanwhile, for carrying out a test based on a method for culturing air-borne microbes, a product which comprises a collecting apparatus in an impactor style and includes an installable medium cassette carrying a capturing carrier that consists of an agar (polysaccharide) culture medium in a gel phase is commercially available (i.e., M Air T type air sample manufactured by Millipore Company). However, an air sampler which can be applied for the ATP method is not commercially available. When the ATP method is applied for testing air-borne microbes, it can be considered that an air sampler in an impactor style for a culture method is used for capturing microbes in a capturing carrier, the captured microbes are recovered from the capturing carrier and dispersed in a suspension, and the microbial counting is carried out based on the ATP method using a reagent kit for detecting a biological luminescence reaction, such as Lucifer HS set.

However, the capturing carrier which consists of a gel phase agar medium and is used for an air sampler in a conventional method (i.e., a combination method for an air sampler and the ATP method) is used under the purpose of culturing captured microbes on the capturing carrier itself. As such, a process of recovering the microbes from the capturing carrier (herein after, referred to as a "recovery process") has not been considered in the conventional method. For the recovery process, there are problems as follows. Specifically, a gel phase capturing carrier is advantageous for capturing the microbes, however, taking out the microbes from the capturing carrier is difficult, so that recovery rate of microbes is poor. Meanwhile, if an agar gel is heated, it can be transformed into a sol phase which can be handled practically the same as a microbial suspension.

However, since high temperature of more than 80° C. is required for the transformation of an agar gel to a sol, most of viable microbes would be damaged or killed during the process. As a result, there are problems that recovery rate of microbes is poor and viable microbes and non-viable microbes cannot be differentiated from each other. Depending on the types of bacteria, inactivation or cell death may occur at the temperatures above 40° C. Under the circumstances, in order to increase the recovery rate of viable microbes, a mild condition which includes repetition of adding a solution having the temperature near the room temperature is added to a gel without transforming an agar gel into a sol and recovering the microbes that are transferred to the solution as microbial suspension is necessary. However, this method still requires a time-consuming and delicate human work by a skilled person, and it cannot be automated, has poor reproducibility and a risk of giving a false positive result due to contamination originating from human workers.

Meanwhile, although a great amount of a solution can be used for recovery to simplify working processes, when the amount of microbial suspension is large, microbial count per unit volume of liquid (i.e., concentration) becomes lower so that the use efficiency of the microbes during measuring process will be consequently lower. For example, the amount of a sample liquid for carrying out the protocols (previous protocols) of Lucifer HS set by Kikkoman Corp., which is the representative product for the ATP method, is 0.1 mL.

Therefore, when the volume of microbial suspension is 1 mL, use efficiency of the suspension during the measurement process is 10%, and it will be 1% when the volume is 10 mL, indicating that the use efficiency of the suspension becomes lower as the volume of the microbial suspension increases. As such, this method has a problem that convenience and use efficiency cannot be achieved at the same time.

In addition, only 1/10 of a sample liquid is actually used for luminescence measurement according to the conventional protocol, there is a problem that overall use efficiency is again only 10% of the recovery rate of the microbes. Further, there is another problem that when extremely small amounts of air-borne microbes (i.e., several to several tens of microbes) are to be measured in a highly clean environment such as a clean room, low recovery rate or low use efficiency may cause an omission error in microbial counting, yielding a false negative result. In order to avoid such omission error, sampling volume of an air sample should be increased and other measures should be also taken. As a result, problem still remains that sampling time is long and results cannot be obtained in short time.

As such, if the above described method is automated as it is, a system construction becomes complicated and a solution required for recovery should be used in more excessive amount to leave a margin, resulting in even lower use efficiency. In addition, when this method is applied to an actual sample, a great amount of contaminants are included in a collected sample in addition to microbes. In this regard, the conventional method is problematic in that a reaction for eliminating ATP, a reaction for extracting ATP, and an ATP luminescence reaction are affected by the contaminants so that measurement accuracy is poor.

In addition, some of microorganisms are present in a state of a spore which is wrapped by a spore membrane having high endurance to chemical substances or heat. Thus, various reactions including the ATP method cannot easily occur. In order to solve such problems of a spore-forming microbe, it has been suggested that a germination inducing factor is first added and then germination is allowed to occur, followed by carrying out various further reactions. For example, according to Japanese Patent Application National Publication (Laid-Open) No. 2001-511356, it is described that germination is allowed to occur in a culture medium comprising a germination factor. In addition, according to Japanese Patent Application Laid-Open (JP-A) No. 2002-330740 and JP-A No. 2004-2229, it is described that germination inducing factor is added first and then germination of a microbe is allowed to occur, followed by sterilization. According to Japanese Patent Application National Publication (Laid-Open) No. 2005-516213, it is described that a germination inducing factor is added and species-specific cell spores are detected and quantitated. According to JP-A No. 2006-174751, it is described that by adding alanine to a cell, strength of the spores of a spore forming microbe is reduced to facilitate the counting of spore forming microbes. According to JP-A No. 2005-253365, a method is described by which microorganisms are admixed with a germination inducing factor and then genes are eluted from them.

Thus, to have a reaction with spore, addition of a germination inducing factor is effective and even for the test based on the ATP method, it is expected that adding germination inducing factor is an effective thing to do.

However, for the ATP method in which various reagents including an ATP eliminating agent, an ATP extracting agent, and a luminescent reagent are added for the reaction, further addition of a germination inducing factor can make the test more cumbersome and can yield a longer test time. Especially, as the reaction with a germination inducing factor takes a relatively a long period of time, the test time becomes longer, making its on-line introduction to a production line difficult.

In addition, when a subject to be tested by the ATP method is an air-borne microorganism, it should be captured in a capturing carrier and then later recovered from the capturing carrier. Time is also required for such process, thus it is problematic in that a long period of time is required from capturing to testing.

SUMMARY OF THE INVENTION

The present invention, which is devised in view of the above described circumstances, has an object of providing a capturing carrier by which air-borne microorganisms can be captured and tested conveniently and quickly, a capturing device using the capturing carrier, an analysis system using the same and a method for capturing and testing microorganisms. In addition, the present invention provides a capturing carrier of microorganisms and capturing device using the same and an analysis system having the same, and a method for capturing and testing microorganisms, which can solve at least one problem of neglecting a process of taking out microbes from a capturing carrier, poor recovery rate or poor use efficiency, low credibility in microbial counting when microbes are present in an extremely small amount, difficulty in automation and a need for a complicated constitution, low accuracy of measurement as a result of contaminant incorporation and the like, all the problems associated with the application of the ATP method to testing of air-borne microbes.

For the achievement of this purpose, the capturing carrier related to the present invention is characterized in that, as a capturing carrier to capture air-borne microorganisms, it comprises a polymer which undergoes a phase transition between gel and sol phase in the temperature range between 15° C. and 40° C. In addition to the polymer, it may further comprise alcohols having no bactericidal activity. Further, the polymer is preferably any one of gelatin or NAGAm/MB-PDA.

Next, the capturing carrier of the present invention is characterized in that, it is a capturing carrier which can capture air-borne microorganisms and consists of a polymer which is in a gel phase at the time of capturing microorganisms but undergoes a phase transition under heating to a sol phase at or less than 40° C., i.e., a thermosensitive polymer, and by containing a test reagent in said polymer said test reagent is eluted upon said phase transition from a gel phase to a sol phase. According to this construction, since a polymer which constitutes the capturing carrier is in a gel phase at the time of capturing, air-borne microorganisms can be efficiently captured. In addition, since the phase transition occurs by heating the capturing carrier at or less than 40° C., the microorganisms can be easily suspended in a solated polymer and then recovered without destroying the microorganisms captured in the capturing carrier. Furthermore, as the gel phase polymer contains the test reagent, which is eluted upon phase transition to a sol phase, the test reagent can be added to the microorganisms simultaneously when they are recovered from the capturing carrier. Therefore, according to the present invention, a process of recovering microorganisms from a capturing carrier and a process of adding a test reagent can be simultaneously carried out. Thus, with the capturing carrier of the present invention, by which air-borne microorganisms can be captured and then recovered from the capturing carrier and a test reagent can be added for measurement, processes from capturing to testing of the air-borne microorganisms can be carried out conveniently in short time.

The capturing device for capturing microorganism related to the present invention is characterized in that it comprises, the capturing carrier comprising a polymer which undergoes a phase transition between a gel and a sol in the temperature range between 15° C. and 40° C., and a vessel to contain the capturing carrier.

An analysis system related to the present invention is characterized in that it comprises a holding member which holds the capturing carrier comprising a polymer (hereinafter, may referred to as a thermosensitive resin) which undergoes a phase transition between a gel and a sol in the temperature range between 15° C. and 40° C., a temperature controlling apparatus which controls the temperature of the capturing carrier, and an air stream controlling part which introduces air flow to the capturing carrier. The temperature controlling apparatus allows switch between the heating and the cooling of the first member before and after the introduction of air flow to the capturing carrier. Regarding the capturing carrier, the gel phase polymer is placed on the filter for filtering a sol and the capturing carrier comprises a grid plate holding part which holds a grid plate constituting a filtration apparatus in combination with the filter, and the filtration apparatus is designed to filter the polymer that is transformed into a sol by the temperature controlling apparatus.

Further, it may comprise a device comprising a capturing carrier which consists of a polymer consisting of a thermosensitive resin which undergoes a phase transition between a gel and a sol in a temperature dependent manner, preferably a thermosensitive resin which undergoes a phase transition between a gel and a sol at 40° C. or less, preferably in the temperature range between 15° C. and 37° C., and a temperature controlling apparatus, and also preferably a filtration apparatus, and if necessary, a dilution apparatus. With a temperature controlling apparatus, the capturing carrier consisting of a polymer (i.e., thermosensitive resin) is maintained in a gel phase to collect air-borne microbes, and then the capturing carrier is subjected to a phase transition to a sol phase by a temperature controlling apparatus or it can be diluted with a dilution solution to yield microbial suspension.

Because the phase transition temperature of the thermosensitive resin material of the present invention is 40° C. or less, capturing and recovery of the microbes are carried out under a mild temperature condition. As to the microbial suspension, ATP of the microbes can be measured by applying a conventional ATP method. Alternatively, and preferably, the microbial suspension is filtered to collect the microbes contained in the microbial suspension on a filter, and then ATP measurement is carried out according to a measurement protocol of a modified ATP method, followed by determination of air-borne microbes.

Thus, according to the capturing device or the analysis system related to the present invention, at least one effect including easiness of taking out, or recovery, the microbes from the capturing carrier, high recovery rate or high use efficiency, high credibility in microbial counting when microbes are present in an extremely small amount, easiness of establishing an automation with simple constitution, and high accuracy of measurement even under the influence by contaminant incorporation and the like can be achieved.

The capturing and test method related to the present invention is characterized in that it comprises steps of capturing microorganisms by which air-borne microorganisms are captured in a capturing carrier by spraying air comprising air-borne microorganisms to the capturing carrier which consists of a polymer in gel phase and contains a test reagent, and taking out and adding by which the capturing carrier is heated at 40° C. or less for a phase transition to a sol phase so that the microorganisms captured in the capturing carrier are recovered from the capturing carrier and at the same time the test reagent is eluted from the capturing carrier, which has undergone a phase transition to a sol phase and then added to the microorganisms above. Thanks to such constitution, recovery of the microorganisms from the capturing carrier and adding a reagent for testing to the microorganisms can be carried out simultaneously. As a result, the operational process becomes easier and less time will be required therefor.

Thus, according to the constitution of the present invention, since the capturing carrier consists of a polymer which undergoes a phase transition from a gel to a sol at 40° C. or less and the test reagent is contained in the polymer, by heating the capturing carrier it undergoes a phase transition from a gel to a sol, and the captured microorganisms are taken out of the capturing carrier and at the same time the test reagent is eluted and added thereto. As a result, less effort and time will be required for the operational processes from capturing to testing of the microorganisms.

BRIEF DESCRIPTION OF THE DRAWINGS

FIG. 4 is a view which shows the measured luminescence value depending on composition of an ATP eliminating agent of a model capturing carrier, according to the first embodiment of the present invention.

FIG. 5 shows the temperature and filtering properties of a model capturing carrier depending on gelatin composition, according to the first embodiment of the present invention.

FIG. 6 shows the temperature and filtering properties of a model capturing carrier depending on glycerol composition, according to the first embodiment of the present invention.

FIG. 7 is a view which shows the comparison of a recovery property between the first embodiment of the present invention and the conventional method example.

FIG. 10 shows the comparison of a property of a capturing carrier having different synthetic polymers, according to the third embodiment of the present invention.

DETAILED DESCRIPTION OF THE PREFERRED EMBODIMENTS

Herein below, with reference to the drawings attached herewith, preferred embodiments of a capturing carrier, a capturing device, a capturing apparatus, an analysis system using the same, and a method for capturing and testing microorganisms, of the present invention will be explained. However, it should be noted that the embodiments are only an example showing the implementation of the present invention, and the technical scope of the present invention is not limited thereto.

The First Embodiment (1) With Respect to the Capturing Device

Figure 1:
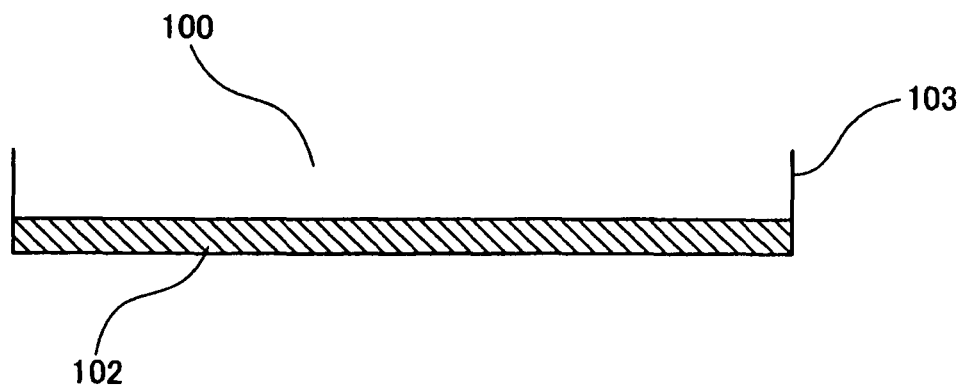
FIG. 1 is a sectional view which shows the brief constitution of the capturing device (100) according to the first embodiment of the present invention.

Brief constitution of the capturing device 100 according to the first embodiment of the present invention is given first. FIG. 1 is a sectional view which shows the brief constitution of the capturing device 100 according to the first embodiment of the present invention. The capturing device 100 comprises a vessel 103 and a capturing carrier 102 housed therein.

As a material for the capturing carrier 102, a resin having the following composition is used in the present embodiment. Specifically, 50% by weight of glycerol, 7.5% by weight of a thermosensitive resin material (i.e., gelatin (hydrolysates of a protein) for the present embodiment will be explained in greater detail below) and 0.03% by weight of an ATP eliminating agent are used and the remaining is balanced with a physiological saline solution. In addition, as a vessel 103, a polystyrene petri dish having a cylinder-shaped concave region with diameter of 40 mm and depth of 5 mm is used.

Next, a method for forming the capturing carrier 102 according to the present invention is explained. By mixing the materials for the capturing carrier 102, under heating if necessary, a homogenous sol is obtained. Operations following this step are carried out under a sterile environment. While heating, the sol is sterilized by filtration with a syringe filter having pore diameter of 0.22 micron. 1 ml of thus obtained sterilized sol is aliquoted and then injected homogeneously to the bottom of the sterilized vessel 103. After cooling it at 4° C., a homogeneous gel is obtained. As a result, the capturing carrier 102 also has an approximate cylinder shape and its diameter is 40 mm and thickness is about 0.8 mm, same as those of the concave region of the vessel 103. Although the capturing carrier 102 is in gel phase at room temperature (25° C.), at an increased temperature it undergoes a phase transition from a gel to sol with the phase transition temperature, therefore it is in a sol phase at 37° C. Thus, the capturing carrier 102 functions as a thermosensitive resin having an upper critical solution temperature (UCST: below this temperature it is present in a gel phase), and its UCST is higher than 25° C. and lower than 37° C. The temperature dependent sol-gel phase transition of the capturing carrier 102 is reversible. In addition, as a capturing carrier, a carrier having lower critical solution temperature can be used (i.e., it is in gel phase at the temperature higher than the corresponding temperature; this type of carrier will be explained later). In this case, for capturing and recovery of the microbes, the conditions for a sol and a gel are adjusted (by employing a reversed temperature condition).

(2) With Respect to the Capturing Apparatus

Figure 2:
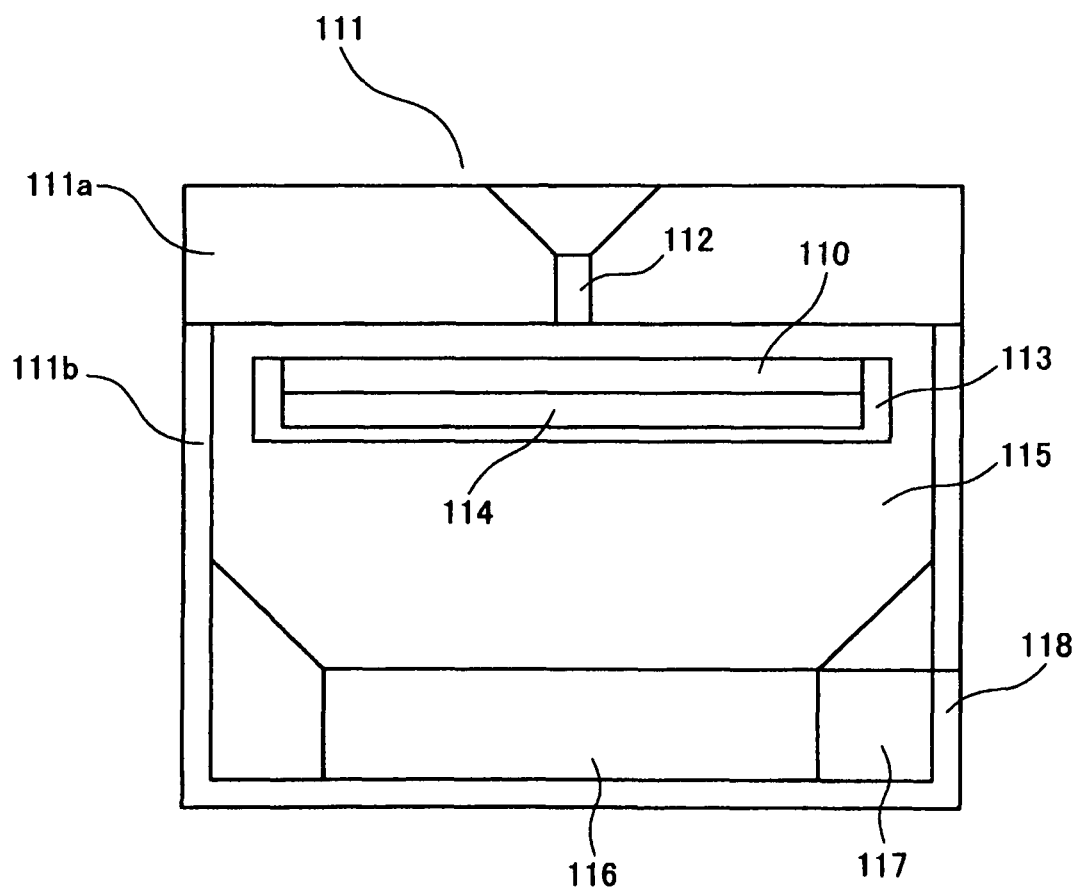
FIG. 2 is a schematic drawing which shows the brief constitution of the capturing apparatus according to the present invention.

Brief constitution of the capturing apparatus 111 according to the present invention is given in view of FIG. 2. FIG. 2 is a schematic drawing which shows the brief constitution of the capturing apparatus 111. The capturing apparatus 111 comprises an upper member 111a, a lower member 111b, an air suction nozzle 112, a holder 113, a temperature control apparatus 114, a pump 116, an exhaust duct 117 and an exhaust filter 118. Within the apparatus, avoid (an empty space) 115 is formed. According to this capturing apparatus 111, the upper member 111a can be detached from the lower member 111b. By attaching the upper member 111a to the lower member 111b to form the capturing apparatus 111, joint region between them becomes air-tight and the external open port of the capturing apparatus 111 corresponds to the air suction nozzle 112 of the upper member 111a, and the exhaust filter 118 of the lower member 111b. In addition, within the lower member 111b, each of the holder 113, the pump 116, and the exhaust filter 118 are fixed. Further, although not graphically shown, a control system or a power supply for the pump 116 or the temperature control apparatus 114 are housed inside the apparatus and operating buttons, a handle and the like are attached on the external surface of the apparatus. Further, the holder 113 comprises the temperature control apparatus 114 and also the detachable capturing device 100. Thus, when the capturing device 100 is attached thereto, the upper side of the temperature control apparatus 114 is in contact with the lower side of the capturing device 100. Within the capturing apparatus 111, the void 115, which connects the exit of the air suction nozzle 112 to the entrance of the pump 116 via the capturing device 100, is formed. In addition, the exit of the pump 116 is closely connected to the exhaust filter 118 via the exhaust duct 117. So called impactor-style capturing apparatus according to the present embodiment has a high flow amount of a sample air, thus it has an advantage of absorbing a certain amount of sample in short time and capturing airborne microorganisms therefrom. In addition, although a one-hole type constitution is envisaged as the air suction nozzle 112 in FIG. 7, the air suction nozzle 112 that can be used for the present invention is not limited to such constitution, and various air suction nozzles including multi-hole type having many small holes, etc. can be used.

Figure 3:
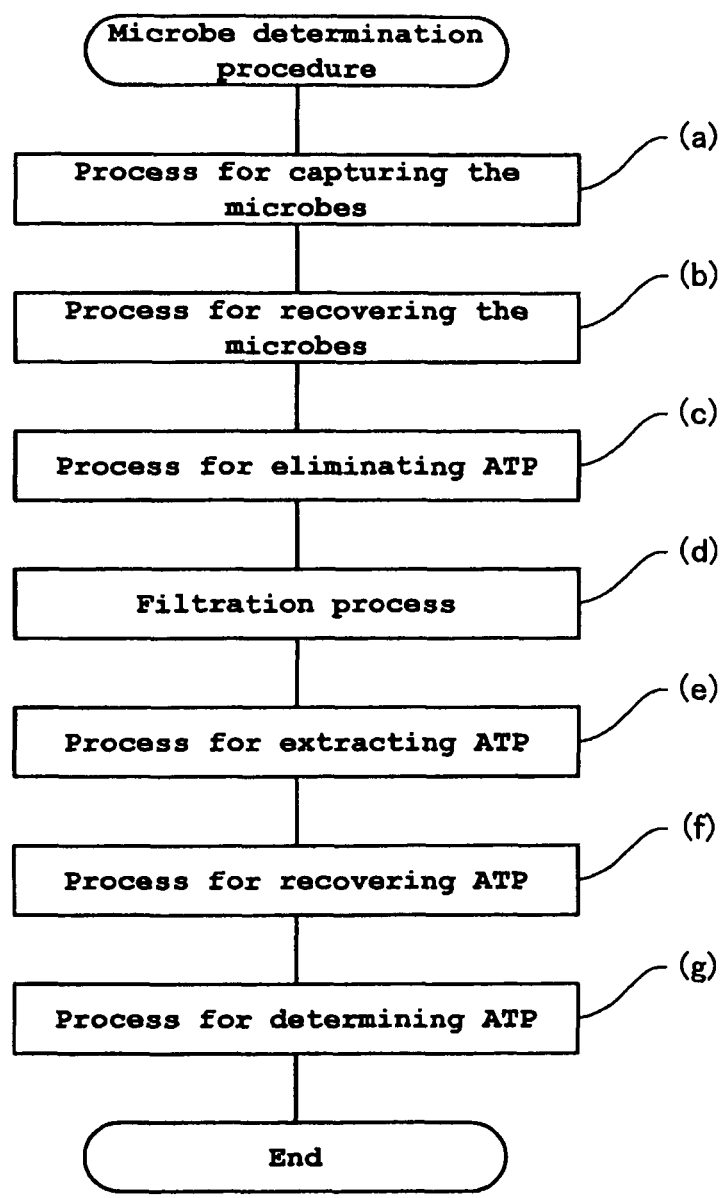
FIG. 3 is a flow chart which shows the determination procedure of microbes according to the first embodiment of the present invention.

(3) With Respect to the Determination Procedure of Microbes (i) First, brief constitution of the determination procedure of microbes according to the present invention is given in view of FIG. 3. The procedure of determining microbes comprises the process (a) of capturing microbes, the process (b) of recovering the microbes, the process (c) of eliminating ATP, the process (d) of filtering, the process (e) of extracting ATP, the process (f) of recovering ATP and the process (g) of determining ATP.

With respect to the process (a) of capturing microbes, air-borne microbes are captured in the capturing carrier 102 (in a gel phase in this case) of the capturing device 100 by using the capturing apparatus 111.

With respect to the process (b) of recovering microbes, the capturing carrier 102 is subjected to a phase transition from a gel phase to a sol phase to obtain microbial suspension (i.e., a sample).

With respect to the process (c) of eliminating ATP, ATPs originating from substances other than the microbes of the sample, i.e., extracellular ATPs or ATPs contained in non-viable microbes, are eliminated.

With respect to the process (d) of filtering, the sample is filtered to remove soluble components or contaminants such as solid components having smaller diameter than the microbes, and the viable microbes contained in the sample are captured on the filter.

With respect to the process (e) of extracting ATP, cell membrane of the microbes is lysed so that the ATPs contained in the cytoplasm of the viable microbes are extracted into a sample solution.

With respect to the process (f) of recovering ATP, a sample solution, including the ATPs that are extracted from the microbes, is obtained.

With respect to the process (g) of determining ATP, a biological luminescence reaction is carried out based on the ATPs contained in the sample solution. Then, by determining the luminescence output by using a luminometer, the ATP content in the sample is obtained and the test result is given in terms of the count of the air-borne microbes contained in unit volume.

(ii) Next, the operation of each constitutional element of the present invention is explained in greater detail in accordance with the determination procedure. Before the process (a) of capturing the microbes, the capturing device 100 is manufactured according to the method described above. After sterilizing the upper member 111a of the capturing apparatus 111 by autoclave, it is transferred to a clean bench which is placed near the region from which air to be determined is captured (herein after, referred to as a "capturing area"), together with the lower member 111b or the capturing device 100 which has been manufactured according to the method described in the above. All the operations in the clean bench are carried out in a sterile manner. The holder 113, the void 115 or the external surface of the lower member 111b are sterilized by using ethanol for disinfection and the like, the capturing device 100 is installed on the holder 113, and then the sterilized upper member 111a is attached thereto to produce the capturing apparatus 111. A sterile cap (not shown), which protects the air suction nozzle 112 of the capturing apparatus 111 from the microbial contamination is further attached, and then the capturing apparatus 111 is taken out from the clean bench. After installing the apparatus in the capturing area, it is ready for the measurement. In this case, the capturing area and the clean bench are maintained at the room temperature of about 25° C. by air-conditioning, and the temperature of each member is also about 25° C. In addition, by running the temperature control apparatus 114, the temperature is set at 25° C. Since the capturing carrier 102 of the capturing device 100 comprises a thermosensitive resin material having the UCST of higher than 25° C. but lower than 37° C., it is present in a gel phase at this temperature.

With respect to the process (a) of capturing microbes, by running the capturing apparatus 111 air-borne microbes present in the capturing area are absorbed and captured in the capturing device 100. Specifically, by running the pump 116, the air outside the capturing apparatus 111 is absorbed into the pump 116 via the air suction nozzle 112 and the void (an empty space) 115. Further, via the exhaust duct 117 and the exhaust filter 118, the air is eventually released to the outside of the capturing apparatus 111. During this process, the air-borne microbes are transferred along with an air stream which passes through the air suction nozzle 112 and collides with the capturing device 100 in approximately vertical direction, and as a result, the microbes collide with the gel phase capturing carrier 102 due to an inertia force and captured. Air or particulates having a weight smaller than the microbes collide with the capturing carrier 102, and then change their direction parallel to the surface of the capturing carrier 102 to get transferred to the void 115, the pump 116, the exhaust duct 117 and the exhaust filter 118. The particulates having a weight smaller than the microbes are captured in the exhaust filter 118 and clean air free of any particulates is released to the outside of the capturing apparatus 111 via the exhaust filter 118. According to the present embodiment, the pump 116 provides with a constant flow amount of 200 L/minute and with the capturing time of 15 minutes a constant amount of air (i.e., three cubic meters) is absorbed. As a result of these processes, air-borne microbes contained in three cubic meters of air are captured in the capturing carrier 102.

With respect to the process (b) of recovering the microbes, by operating the temperature control apparatus 114, its temperature is increased from 25° C. to 37° C. From the top surface of temperature control apparatus 114 to the bottom surface of the capturing device 100, i.e., to the vessel 103 and also to the capturing carrier 102, heat is transmitted, resulting in fast increase of the temperature of the capturing carrier 102 to 37° C. The capturing carrier 102 adopted for the present embodiment functions as a thermosensitive resin having UCST higher than 25° C. but lower than 37° C., therefore, the resin undergoes a phase transition from a gel phase to a sol phase by temperature increase from 25° C. to 37° C. The particulates including the viable microbes and the like that are captured in the capturing carrier 102 become dispersed in this sol, and as a result, microbial suspension is obtained. In addition, water soluble components that are other than the viable microbes and the like, captured in the capturing carrier 102, are dissolved in the sol. As a result, 1 mL sample of the microbial suspension is recovered in the vessel 103.

With respect to the process (c) of eliminating ATP, after adding 30 μL of the ATP eliminating agent that is included in Lucifer HS set to the sample of the microbial suspension, the resulting mixture is maintained at room temperature for 30 minutes. With this process, ATPs not originating from the viable microbes of the sample, i.e., extracellular ATPs or ATPs contained in non-viable microbes, and extremely tiny amount of the ATP present in the capturing carrier 102 are all removed. As a result of this process, 1.03 mL reaction solution, from which ATPs originating from other than viable microbes are removed, is obtained in the vessel 103.

Before the filtration process (d), a filtration device, (not shown) in which the membrane filter (HAWP 02500, manufactured by Millipore Company, the diameter is 25 mm, the membrane is made of MF-Millipore and the pore diameter is 0.45 micron) is mounted on top of a grid plate, is prepared in advance by sterilization with autoclave.

With respect to the filtration process (d), the reaction solution is added dropwise to the upper side of the filter and by suctioning the bottom surface (i.e., grid plate surface) under reduced pressure, the filtration is carried out. After the completion of the filtration, the bottom side of the filter is brought back to the atmospheric pressure. As a result of this process, water soluble components or contaminants such as solid components other than microbes which have a diameter smaller than 0.45 micron that are contained in the reaction solution are filtered, and the filtration device comprising the filter capturing the viable microbes (larger than 0.45 micron) is obtained.

With respect to the process (e) of extracting ATP, 100 μL of the ATP extracting agent that is included in Lucifer HS set is added to the upper side of the filter of the filtration device, and then mixed at room temperature for 20 seconds. Since the filter is mounted on the O-ring consisting of silicone rubber, for example, and the bottom surface of the filter is exposed to an atmospheric pressure, no filtration can occur. Instead, the added reagent solution stays on the filter due to surface tension. As a result, the cell membrane of the viable microbes is lysed and the ATPs contained in the cytoplasm of the microbes are extracted. Consequently, 100 μL sample solution comprising the ATP is obtained on the filter.

With respect to the process (f) of recovering ATP, 30 μL of the d sample solution is taken by using a pipette. As a result of this process, out of 100 μL of the sample solution comprising the ATP of the viable microbes, 30 μL are obtained as a recovery solution in the pipette. Since 30% of the ATPs contained in the viable cells that are present in the captured sample are recovered as a recovery solution, the use efficiency for the recovery solution is 0.3 for this case.

Before the process (g) of determining ATP, 0.2 mL of the ATP luminescent reagent is injected to a polypropylene test tube for a luminometer, and then installed in the luminometer (Berthold Detection Systems, FB12) to determine the luminescence output (i.e., baseline). The luminescence output for the baseline is approximately 40 to 60 cps (count per second). Next, 200 amol of the standard sample (10 μL of the ATP standard solution with the concentration of 20 pmol/L) is further injected to the test tube which comprises 0.2 mL of the ATP luminescent reagent. After mixing, the luminescence output is determined (standard sample). The luminescence output of the standard sample is approximately 2000 cps. Effective luminescence output of the standard sample is obtained by subtracting the luminescence output of the base line from the luminescence output of the standard sample. Further, by dividing the effective luminescence output of the standard sample with the ATP amount thereof, a slope sensitivity, i.e., the effective luminescence output per unit amount of ATP, is obtained. The slope sensitivity is approximately 10 to 20 cps/amol.

With respect to the process (g) of determining ATP, 30 μL of the recovery solution is further injected to the test tube comprising the above ATP luminescent solution. After mixing, the luminescence output is determined in the same manner (sample) Effective luminescence output of the sample is obtained by subtracting the luminescence output of the base line from the luminescence output of the sample. Further, by dividing the effective luminescence output of the sample with the slope sensitivity, the ATP amount contained in the recovery solution is obtained. By dividing the resulting value with 0.3 (i.e., the use efficiency of the recovery solution), the ATP amount contained in the viable microbes of the sample is obtained. Further, by dividing this ATP amount in the sample with the average value of ATP content per one viable microbe (approximately 2 amol), average count of the viable microbes that are contained in the sample is obtained. Still further, by dividing this average count of the viable microbes that are contained in the sample with the volume of the air sample (i.e., three cubic meters), average count of the viable microbes contained in unit volume of the air sample is obtained. As a result, the ATP content in the sample solution is obtained and the test result is finally obtained in terms of the count of the air-borne microbes per unit volume.

(4) With Respect to the Optimization of the Capturing Carrier

As described above, a constitutional element which is specific to the first embodiment of the present invention can be the capturing carrier 102. As such, optimization of the constitution of the capturing carrier 102 was carried out as follows.

(i) First, the volume of the suction air is three cubic meters, the flow amount of the pump 116 is 200 L/minute and the diameter of the suction nozzle (112) is 0.48 cm in the present embodiment. Under this operational condition, since the linear velocity of the air in the air suction nozzle 112 is 181 m/s in average and the suction air volume is as high as three cubic meters, when a conventional capturing carrier consisting of an agar gel and the like is used, moisture will be evaporated drastically to reduce the volume of the gel and to dry the gel surface. As a result, the gel may turn into a solid state and microbes cannot be captured with good efficiency. Thus, in the present embodiment, the capturing carrier 102 which contains 50% of glycerol is used so as to prevent any deform or drying of the capturing carrier 102. Consequently, a high capturing efficiency for capturing air-borne microbes with the capturing carrier 102 is achieved. As a material to prevent any deform or drying of the capturing carrier 102, in addition to glycerol which is used for the present embodiment, various alcohols such as ethylene glycol and propylene glycol can be used (for the prevention of dryness). In addition, as to the type of the alcohols, they are required to be free of a bactericidal activity. That is because the microbes captured in the capturing carrier 102 are to be saved. For such reasons, ethanol is not suitable, for example.

(ii) As a second optimization of the capturing carrier 102, a capturing carrier made of glycerol, gelatin and a physiological saline solution will be discussed. In this case, there is a confirmed problem that even after filtration an abnormally high value of a determination result is obtained for a blank sample which does not comprise any microbes (i.e., 10 to 20 amol). It is believed that such result is caused by the fact that especially gelatin among the materials for the capturing carrier contains a large amount of ATP compared to the extremely tiny amount of the ATP to be detected (i.e., several amol), the residual ATPs originating from the gelatin may serve as a reason for such abnormally high value.

Under the circumstances, before implementing the present embodiment, a model test as follows is carried out to figure out a method by which the ATP contained in the capturing carrier is removed in advance to lower the blank value. In other words, the pre-treatment is for the removal of the ATPs originating from the gelatin.

Specifically, to a base in which 5% by weight of gelatin and 50% by weight of glycerol are dissolved in a physiological saline solution, the ATP eliminating agent that is contained in Lucifer HS set is added in various mixing ratio to give a model capturing carrier. This model capturing carrier is heated to 37° C. for transition to a sol phase, and 10 µL of the resulting sol as it is or the solution diluted with purified water is aliquoted and added to 0.2 mL of the ATP luminescent reagent. Then the luminescence output is determined. One exemplary result is shown in FIG. 4. When no ATP eliminating agent is added, blank signal is as high as 7178 cps.

Meanwhile, the blank signal for the model capturing carrier in which the ATP eliminating agent is added in an amount of 0.03 or 0.1% by volume, was 103, 57 cps, respectively, showing a dramatic decrease compared with no addition group. The effective luminescence output, which is a difference compared to the value of the baseline comprising pure water as a sample without any ATP (for this experiment, 56 cps), is 7122 (=7178-56), 47 (=103-56), or 1 (=57-56) cps, respectively, for the system comprising the ATP eliminating agent at a concentration of 0, 0.03, or 0.1%, and the ATP content calculated by using the sensitivity of approximately 11.2 cps/amol is about 636, 4.2, or 0.1 amol, respectively.

As such, by adding 0.03% or more of the ATP eliminating agent to the capturing carrier, a capturing carrier, in which ATPs originating from gelatin and the like are effectively decomposed and removed, can be produced. As a result, the influence on the determination result by such ATP is minimized to $\frac{1}{100}$ or less, and with combination of filtration, the above described abnormally high value can be avoided and inhibited to the level at which no substantial influence is exerted thereto.

Based on the above determination results, it was found that as a composition for the capturing carrier 102 containing gelatin, it is preferable to contain the ATP eliminating agent. In addition, it was also found that when the ATP eliminating agent included in Lucifer HS set is used its constitutional amount is to be 0.03% or more. By having this value of 0.03%, which is the minimum value of the essential constitution, as a constitution of the ATP eliminating agent of the present embodiment, ATP contamination which mainly comes from gelatin can be excluded from the capturing carrier 102.

(iii) As a third optimization of the capturing carrier 102, a gelatin composition which is used as the thermosensitive resin material is determined after fixing the constitutional ratio of the ATP eliminating agent in the capturing carrier to 0.03%.

FIG. 5 shows the temperature and filtration properties of a model capturing carrier which is produced with 0.03% of the ATP eliminating agent, 50% by weight of glycerol and balance of physiological saline solution, depending on different concentration of gelatin, i.e., 5, 7.5, and 10% by weight. As it is shown in FIG. 5, in any of the composition, the model capturing carrier is transformed into a sol phase within 5 minutes when the temperature is gradually increased from 25° C. to 37° C., indicating that it can be preferably used for the recovery process. When the gelatin concentration is 7.5% by weight or more, the gel strength is high at 25° C. so that it can be used as a capturing carrier. However, when the gelatin concentration is 5% by weight, the gel strength at 25° C. is slightly weaker.

As such, by having the gelatin concentration 7.5% by weight or more, a thermosensitive resin material which is a gel phase at 25° C. and a sol phase at 37° C., i.e., a material having UCST higher than 25° C. but lower than 37° C. can be obtained.

Meanwhile, with respect to the filtration property under the above described filtration process, when the gelatin concentration is 7.5% by weight or less, 1 mL of the sol can be eluted within 40 seconds, and therefore it can be favorably applied to the filtration process.

However, when the gelatin concentration is 10% by weight, viscosity is too high and the filtration is difficult to carry out. As such, there is a case in which some of the non-filtered components remain on the filter.

From the above results, it was found that, as a material for a capturing carrier, which has UCST higher than 25° C. but lower than 37° C. and good filtration property, the gelatin concentration is preferably between 5% to 10% by weight, and the optimum concentration is 7.5% by weight. Such optimum concentration of 7.5% by weight is adopted as a gelatin concentration for the present embodiment.

(iv) As a fourth optimization of the capturing carrier 102, a glycerol composition is determined after fixing the constitutional ratio of the ATP eliminating agent in the capturing carrier to 0.03%.

FIG. 6 shows the temperature and filtration properties of a model capturing carrier which is produced with 0.03% of the ATP eliminating agent, 5, 7.5, or 10% by weight of gelatin and balance of physiological saline solution, depending on different concentration of glycerol, i.e., 30, 40, 50 and 60% by weight.

As it is shown in FIG. 6, in any of the composition, the model capturing carrier is transformed into a sol phase at 37° C., indicating that it can be preferably used for the recovery process. When the glycerol concentration is 50% by weight or more, the gel strength is high at 25° C. so that it can be used as a capturing carrier.

However, when the glycerol concentration is 40% by weight or less, the gel strength at 25° C. is slightly weaker. As such, by having the glycerol concentration 50% by weight or more, a thermosensitive resin material which has UCST higher than 25° C. but lower than 37° C. can be obtained.

Meanwhile, with respect to the filtration property, when the glycerol concentration is 50% by weight or less, 1 mL of the sol can be eluted within 40 seconds, and therefore it can be favorably applied to the filtration process. However, when the glycerol concentration is 60% by weight, viscosity is too high and the filtration is difficult to carry out. As such, there is a case in which some of the non-filtered components remain on the filter.

From the above results, it was found that, as a material for a capturing carrier, which has UCST higher than 25° C. but lower than 37° C. and good filtration property, the glycerol concentration is preferably between 30% to 60% by weight, and the optimum concentration is 50% by weight. Such optimum concentration of 50% by weight can be adopted as a glycerol concentration for the present embodiment.

(5) With Respect to the Evaluation of Recovery Property

The recovery property of the present embodiment is evaluated with the method as follows. As a model sample of air-borne microbes, suspension which is obtained by dilution of the standard microbes (Easy QA Ball *Escherichia coli* 10,000 cfu distributed by Nissui Pharmaceutical Co., Ltd.) with purified water is prepared. For the process (a) of capturing microbes, a step of capturing air-borne microbes by the capturing apparatus 111 within the capturing device 100 from the air sample is substituted by adhesion of a certain amount of a model sample to the capturing carrier 102. Subsequent steps are carried out according to the evaluation test of the present embodiment. For a comparison, a conventional method in which an agar gel is used as the capturing carrier 102 for the process (a) of capturing microbes, and as a method for recovering the microbes for the process (b) of recovering microbes, 1 mL of physiological saline solution is aliquoted in two divided portions to the surface of the agar gel and then taken back from the surface for recovery, and also a method in which the process (a) of capturing microbes is substituted by adhesion of a model sample, same as the present embodiment, are determined. For the capturing carrier 102 of the conventional method, commercially available agar culturing medium (Tryptic Soy Agar) is used.

FIG. 7 shows an exemplary result of determining a duplicate set based on a model sample having 500 CFU, according to the above described two methods. According to the result of the conventional method, the ATP amount, the average count of viable microbes, and the recovery ratio are very low. Especially for the one of the duplicate set, it gave a result showing absolutely no recovery of the microbes.

Meanwhile, according to the result of the present embodiment, the average ATP amount is approximately 540 amol, the average count of viable microbes is approximately 270 CFU, and the recovery ratio is approximately 55% (=(44+65)/2). These results are almost four times (=55/13) higher than those of the conventional method (i.e., it is more close to the recovery ratio of 100%).

Thus, the embodiment of the present embodiment provides with a highly accurate measurement result compared to the conventional method. The biggest difference between the present invention and the conventional example resides in the capturing device 100 and the process of recovering microbes therefrom. The reason for obtaining high accuracy for the present invention compared to the conventional method is believed to be due to the fact that during the process (b) of recovering microbes, the microbes can be efficiently recovered from the capturing device 100. In fact, after culturing the capturing carrier 102 which was used for the conventional method as a reference (i.e., the remainder obtained after the recovery of the microbes) at 35° C. for two days, it was found that all capturing carriers expressed a number of colonies.

As such, the conventional method showing the result separate from the specific values may be due to the fact that the recovery ratio for the process (b) of recovering the microbes is low.

Meanwhile, by adopting a new method, i.e., the method of the present embodiment in which the capturing carrier itself is subjected to a phase transition from a gel to a sol without any contamination by non-contacting and mild condition including a temperature change under 40° C., which does not cause a damage or death of the microbes by heat, and therefore it can be treated as microbe suspension, the microbes recovered by the capturing carrier can be efficiently provided for the next process.

(6) With Respect to the Evaluation of Overall Property

The overall property of the first embodiment of the present embodiment is evaluated as follows. As a model sample of air-borne microbes, the microbes comprised in the laboratory air are used. Specifically, by using the laboratory air as a sample, the determination of microbes is carried out according to the determination procedure of the present example. For a comparison, the results obtained from a culture method are used. For the culture method, an air sampler by Millipore Company (M Air T type) and an agar culture medium (Tryptic Soy Agar) are used to collect one cubic meter of air according to the manufacturer's guidelines. Thus obtained capturing carrier is cultured at 35° C. for two days and the colony is counted. The results are 950 CFU/m$^3$ and 1100 CFU/m$^3$ for the present embodiment and the culture method, respectively. Both results are in good agreement. Meanwhile, the time spent for the determination is about one hour and 50 hours, respectively, including the time required for the capturing. Thus, the present example according to the present invention is advantageous in that it can provide with a test result having accuracy as high as that of the culture method, but in extremely short time (i.e., approximately 1/50 compared to the culture method).

As it has been described in the above, according to the first embodiment of the present invention, the recovery ratio of the microbes from the capturing carrier is high so that the microbial counting can be carried out with high credibility. In addition, by applying the present embodiment, a highly accurate measurement of viable microbes can be carried out in extremely short time.

The Second Embodiment (1) With Respect to the Capturing Device

Figure 8:
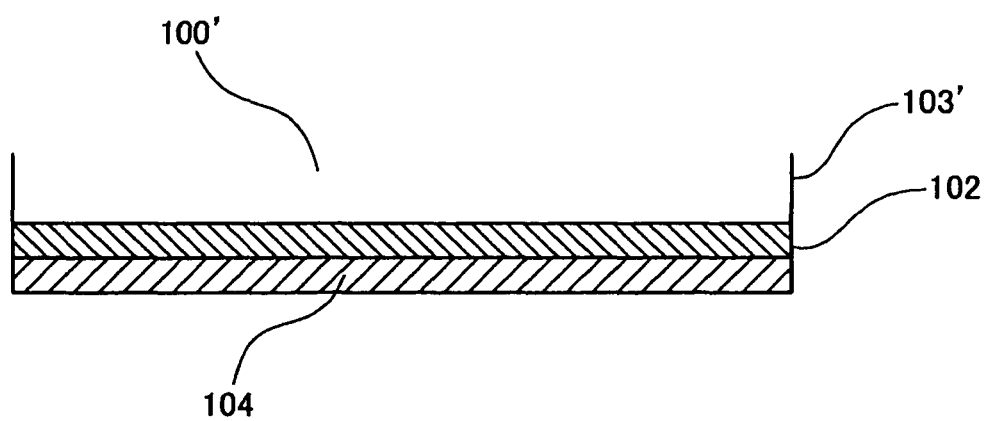
FIG. 8 is a sectional view which shows the brief constitution of the capturing device 100 according to the second embodiment of the present invention.

FIG. 8 is a sectional view which shows the brief constitution of the capturing device 100' according to the second embodiment of the present invention. The capturing device 100' comprises the capturing carrier 102, a vessel wall 103' and the filter 104. The capturing device 100' is formed by adhering the filter 104 which is the same as the one used for the first embodiment to the lower region of the hollow-shaped vessel wall 103' and pouring the source material for the capturing carrier 102, which is produced with the same method as the one used for the first embodiment, over the cooled filter 104. For Filter 104, the membrane filter (HAWA0250) that is the same as the ones used for filtration process (d) of the first embodiment was used.

(2) With Respect to the Analysis System

Figure 9:
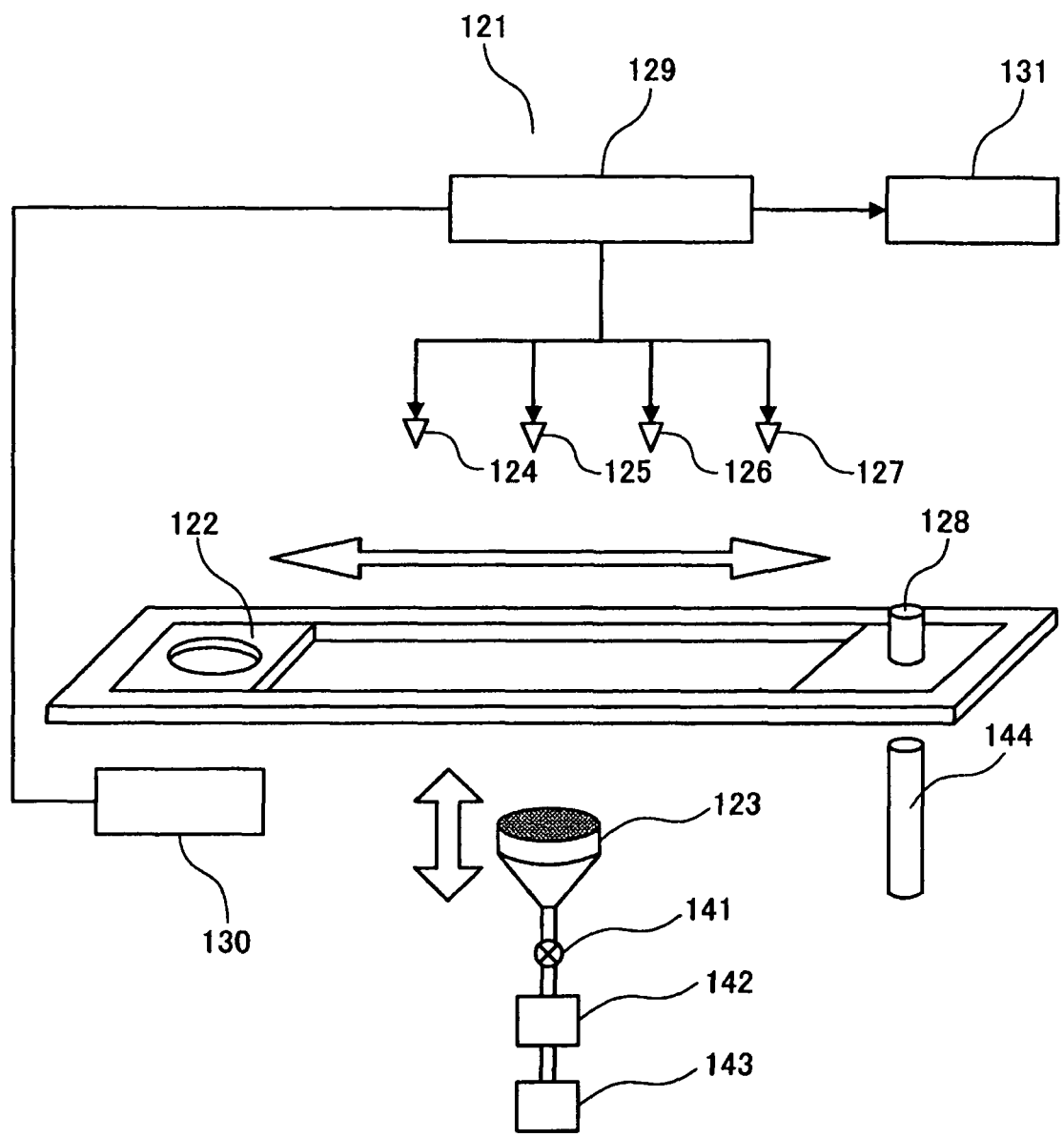
FIG. 9 is a view which shows the brief constitution of the analysis system according to the second embodiment of the present invention.

FIG. 9 is a view which shows the brief constitution of the analysis system 121 according to the second embodiment of the present invention. The analysis system 121 comprises a capturing device holder 122, a grid plate holder 123, a dispenser for the ATP eliminating agent 124, a dispenser for the ATP extracting reagent 125, a pipettor for the recovery of ATP 126, a dispenser for the luminescent reagent 127, a test tube holder 128, a control device 129, a temperature control apparatus 130, a sterilizing apparatus 131, an electronic valve 141, a waste trap 142, a suction pump 143 and the photon counter 144. To each of the capturing device holder 122, the grid plate holder 123, and the test tube holder 128, the capturing device 100', a grid plate and a test tube can be attached (not shown). In addition, each of them carries a transporting means to return each holder to a specific site.

Further, the dispenser for the ATP eliminating agent 124, the dispenser for the ATP extracting reagent 125, the pipettor for the recovery of ATP 126, and the dispenser for the luminescent reagent 127, all carry a means which can be used for automatic operation of dispensing or pipetting of various reagents that are not graphically shown, in accordance to a control signal from the control device 129.

The grid plate holder 123, the electronic valve 141, the waste trap 142, and the suction pump 143 constitute the suction apparatus for filtration in conjunction with the grid plate which is not graphically shown. Further, in combination with the filter 104 at the lower region of the capturing device 100', it forms a filtration apparatus.

The electronic valve 141 and the suction pump 143 are controlled by the control device 129. Under the control by the control device 129, the temperature control apparatus 130 controls the temperature of various regions within the device, especially controls the temperature of the capturing device holder 122 in the range between 37° C. and 40° C. The photon counter 144 determines the luminescence strength released from the test tube (not shown) mounted in the test tube holder 128 in terms of photon count, which is then transmitted to the control device 129.

(3) With Respect to the Measuring Operations

In connection to the above, the operation utilizing the capturing device 100', the capturing apparatus 111 (FIG. 2) and the analysis system 121 of the present invention will be explained. The operation according to the present embodiment is basically the same as that of the first embodiment, except that the analysis system 121 is employed for an automatic operation of the processes from the process (b) of recovering the microbes to the process (g) of determining ATP as shown in FIG. 3. In addition, since the present embodiment is mainly focused on the method for recovering microbes that are captured on the capturing device, detailed explanation regarding the electric system, the control system, the optical system including light shielding, and the device system is not given.

According to the present embodiment, before the initial use of the analysis system 121, inside of the analysis system 121 is sterilized by using the sterilizing apparatus 131, and also ozone gas (in case UV sterilization method is used) or particulates are removed. In addition, even when the analysis system 121 is in use, ozone gas and particulates are continuously removed by using the sterilizing apparatus 131.

For the process (a) of capturing microbes according to the present embodiment, particulates of an air sample are collected on the capturing carrier 102 (in gel phase) of the capturing device 100' at room temperature (25° C.) by using the capturing apparatus 111, similar to the first embodiment.

Before the process (b) of recovering microbes, the temperature control apparatus 130 is run to maintain the temperature of the capturing device holder 122 between 37° C. and 40° C. For the process (b) of recovering the microbes under a sterile condition, the capturing device 100' is installed in the capturing device holder 122 of the analysis system 121. Then, the subsequent processes from the process (b) of recovering the microbes to the process (g) of determining ATP are carried out in a sterile and an automated way under the control of the control device 129. With a work by the temperature control apparatus 130, heat is transmitted from the capturing device holder 122 to the capturing device 100', and further to the capturing carrier 102, resulting in rapid increase in temperature of the capturing carrier 102° C. to 37° C. As the capturing carrier 102 employed for the second embodiment is based on a thermosensitive resin material having UCST higher than 25° C. but lower than 37° C., by increasing the temperature from 25° C. to 37° C., it undergoes a phase transition from a gel phase to a sol phase. As a result of this process, 1 mL sample of the microbial suspension is recovered inside the capturing device 100', i.e., within a space that is formed by the vessel wall 103' and the filter 104.

With respect to the process (c) of eliminating ATP, the capturing device holder 122 having the capturing device 100' is returned to the lower region of the dispenser for the ATP eliminating agent 124, and the ATP eliminating agent is added to the microbial suspension (30 μL) (herein after, all the processes of adding the reagent by a dispenser are carried out in the same manner, and the detailed process including returning process and the like is simply described as "dispensing"). The capturing device holder 122 having the capturing device 100' is returned to the upper region of the grid plate holder 123, and also the grid plate holder 123 having the sterilized grid plate (not shown) is returned to the upper region so that it can fit into the filter 104 located below the capturing device 100, and the grid plate to form the filtration apparatus. By keeping the apparatus for 30 minutes in this state, ATPs not originating from the viable microbes are eliminated. As a result of this process, 1.03 mL of the reaction liquid, from which ATPs not originating from the viable microbes are eliminated, is obtained inside the capturing device 100'.

With respect to the filtration process (d), by running the suction apparatus the bottom side of the filter is exposed to reduced pressure. As a result, the reaction liquid is absorbed and filtrated from grid plate of the filter 104 to the waste trap 142 via the electronic valve 141. Upon the completion of the filtration, the suction apparatus is allowed to stop and the bottom surface of the filter is brought back to atmospheric pressure. As a result of this process, the capturing device 100' having the filter 104 in which the viable microbes in the reaction liquid are captured is obtained.

Before the process (e) of extracting ATP, the grid plate holder 123 is returned to the lower region and the filter 104 which is located below the capturing device 100' is detached from the grid plate, resolving the filtration apparatus.

With respect to the process (e) of extracting ATP, 100 μL of the ATP extracting reagent is added to the top surface of the filter 104 by using the dispenser for the ATP extracting reagent 125, and then mixed at room temperature for 20 seconds. Since the bottom surface of the filter 104 is in atmospheric pressure, no filtration occurs. Further, since the bottom surface of the filter is not in contact with the grid plate, the liquid stays on the filter 104 via surface tension. As a result of this process, 100 μL of a sample solution comprising the ATP, which has been contained in the viable microbes, are obtained on the filter.

With respect to the process (f) of recovering ATP, 30 μL of the sample solution is taken by using the pipettor for recovering ATP (126). As a result of this process, 30 μL out of 100 μL sample solution comprising the ATP, which has been contained in the viable microbes, are obtained as a recovery solution in the pipette. The use efficiency of the recovery solution is 0.3.

Before the process (g) of determining ATP, to the test tube installed in the test tube holder 128 0.2 mL of the ATP luminescent reagent is injected by using the dispenser for the luminescent reagent 127 followed by the measurement of the base line luminescence output. Next, by using a standard sample having 200 amol of ATP, the luminescence output is measured in the same manner for the standard sample. Subsequently, with the same procedure as the first embodiment, the effective luminescence output and the sensitivity of the standard sample are obtained.

With respect to the process (g) of determining ATP, 30 μL of the recovery solution is further added to the test tube comprising the ATP luminescent reagent by using the pipettor for recovering ATP (126), and then the luminescence output of the sample is measured in the same manner. Subsequently, with the same procedure as the first embodiment, the effective luminescence output of a sample, ATP amount in the recovery solution, the ATP amount comprised in the viable microbes of the sample, the average count of the viable microbes in the sample, and the average count of viable microbes comprised in a unit volume of a gas sample are obtained. As a result of this process, the ATP content in the sample solution is measured and the test result is obtained in terms of the count of the air-borne microbes per unit volume.

The biggest difference between the present second embodiment and the first embodiment is whether or not the processes from the process (b) of recovering the microbes to the process (g) of determining ATP are automated. Thus, according to the second embodiment, in addition to the same effect obtainable from the first embodiment, more specific effects including high sensitivity, simplicity, saving of labor forces, avoidance of an artificial mistake, improved reproducibility and the like can be expected by automation.

The Third Embodiment

The third embodiment of the present invention is basically the same as the first and the second embodiment, except that as a thermosensitive resin material for the capturing carrier 102 of the capturing device 100 a synthetic polymer is used.

The thermosensitive resin material used for the present embodiment is a synthetic polymer which undergoes a phase transition between gel and sol near the room temperature. Following two types of materials are compared to each other.

(A) Mebiol Gel MB-10 manufactured by Mebiol Inc., having the lower critical solution temperature (LCST) of about 20° C.

(B) Copolymer of N-acryloylglycineamide (NAGAm) and N-methacroyl-N'-biotinylpropylenediamine (MBPDA) (10:1 ratio, herein after abbreviated as NAGAm/MBPDA), having the UCST of about 22° C.

Further, NAGAm/MBPDA that is synthesized according to the method described in "New Sciences of Dispersion and Emulsification and Development of New Application Techniques" (Edited by Furusawa Kunio, ISBN4-924728-50-0, Techno System Company, p. 370, 2006) is used for the present invention.

After preparing the capturing carrier 102 comprising 4% by weight of the above described two types of a synthetic polymer, it is subjected to sterilization by autoclave at 120° C. for 20 minutes followed by ATP degradation. Properties of the resulting carrier are then determined and summarized in FIG. 10. After maintaining under the condition (1) of FIG. 10 for more than one night, by observing a change in gel-sol phases in accordance with a change in temperature from (2) to (3), the temperature property is determined. Specifically, whether or not the synthetic polymer which experienced a condition change from 15° C. to 37° C. can go back to the original state of 15° C. when the temperature is brought back to 15° C. is followed. As it is indicated in FIG. 10, MB-10 is in a gel or a sol phase under the condition of (2) and (3), respectively, and this process follows the phase transition in accordance with the definition of LCST (i.e., a sol below the transition temperature and a gel above the transition temperature).

However, under the condition (1) of the FIG. 10, it is present in a soft gel phase, indicating a problem of a hysteresis or a time-dependent deviation from the LCST.

Meanwhile, NAGAm/MBPDA is in a gel or a sol phase under the condition of (1) and (3), (2) of the FIG. 10, respectively, indicating the phase transition according to the definition of UCST (i.e., a gel below the transition temperature and a sol above the transition temperature).

As such, in terms of the temperature property, it is considered that NAGAm/MBPDA is favorable than MB-10. Such results are observed when the concentration of NAGAm/MBPDA is in the range between 1% and 10% by weight.

Next, the filtration property of NAGAm/MBPDA is evaluated. For the evaluation of the filtration property, the capturing carrier 102 is heated to 37° C. to transform into a sol phase and the pressurizing filtration (i.e., filtration under positive pressure) using a syringe filter having the pore diameter of 0.45 μm, or, the de-pressurizing filtration (i.e., suction filtration, or filtration under negative pressure) using a membrane filter having the pore diameter of 0.45 μm are carried out. As a result, although the pressurizing filtration was possible, the de-pressurizing filtration could not be performed when NAGAm/MBPDA was present as it is (i.e., a sol phase in 4% by weight).

Thus, the sol was diluted with purified water and used to test the possibility of de-pressurizing filtration. As a result, it was found that with ⅓ dilution (i.e., 1.3% by weight), the de-pressurizing filtration can be carried out, but not with ½ dilution (2% by weight). Furthermore, by increasing the dilution ratio to lower the viscosity of the sample solution, passive filtration using an absorption pad placed on the back side of the filter can be also employed instead of the suction filtration.

As a result of the above determination, it is found that a thermosensitive resin based on a synthetic polymer can be used for the capturing carrier 102 of the capturing device 100 of the present invention, and in particular, the capturing carrier 102 which contains 1% to 10% by weight, more particularly about 4% by weight, of NAGAm/MBPDA represents the UCST of between 15° C. and 37° C., and thus can be preferably used.

The biggest difference between the present third embodiment and the first embodiment is that, by using an apparatus which can set the temperature at 15° C. for the process (a) of the capturing microbes, the temperature of the capturing carrier 102 is adjusted to 15° C. to transform it into a gel phase and then the microbes are captured, and for the filtration process (d) the filtration is carried out following the dilution of the capturing carrier 102 in a sol phase or the pressurizing filtration is carried out without any dilution.

According to the present third embodiment, the synthetic polymer used as a thermosensitive resin material is highly stable and homogeneous properties can be obtained in high reproducibility, and therefore the production cost can be reduced in accordance with a mass production. In addition, because the viable microbes originating from the source material can be sterilized by autoclave, ATPs originating from the source material can be also removed by autoclave (i.e., without using any ATP eliminating agent).

Summary of the First to the Third Embodiment

The capturing device of the present invention can collect air-borne microbes by using a gel phase capturing carrier. Thus, the capturing property is equivalent to that of a capturing carrier of prior art. In addition, since the capturing carrier is subjected to a phase transition to a sol phase and then used as it is or after the dilution if necessary, it can be handled practically in the same manner as the microbial suspension. Consequently, a process of taking out the microbes from the capturing carrier can be omitted, and therefore incomplete taking out of the microbes during the taking out process or loss due to the damaged microbes and the like can be avoided.

Further, since the temperature condition for the capturing and the recovery of the microbes is mild (15° C. to 37° C.), a problem associated with the damage or loss of the microbes by heat does not occur. As a result, achievement of a very high recovery rate is also expected.

Further, a complicated process of taking out the microbes can be replaced by a simple process of changing the temperature only, or with a combination of changing the temperature and the dilution, various effects including automation, simplification of a system constitution, facilitation of the processes, improvement of the reproducibility, lowering a risk for contamination and the like can be obtained.

Further, because the volume of the microbial suspension is small, the concentration and the use efficiency of the microbes are high. In addition, the microbes comprised in the microbial suspension are collected on the filter by filtration and the like, the liquid volume can be substantially reduced to zero so that the concentration and the use efficiency of the microbes are extremely high.

Still further, the credibility is high since the influence by water-soluble or small-sized contaminants can be excluded. As such, there is an advantage that determination of the microbes can be carried out in a highly sensitive, highly accurate and an automated way. In addition, the measurement accuracy and sensitivity are high for testing the air-borne microbes, and the results can be obtained conveniently in short time.

The Fourth Embodiment

Next, the fourth embodiment of the present invention will be explained. Regarding the constitution of the capturing apparatus of the present embodiment, the capturing apparatus that is the same as the one used for the first to the third embodiment (FIG. 2) is appropriately used.

The capturing carrier 102 of the present embodiment contains a test reagent in a gel phase polymer. This test reagent is designed to get eluted and added when the polymer undergoes a phase transition to a sol phase. Furthermore, the test reagent is selected depending on the type of the microorganisms or the test method to be taken. For example, when a test based on the ATP method is carried out, an ATP eliminating agent, a germination inducing factor, an ATP extracting agent, a luminescent reagent and the like are selected.

The capturing carrier 102, as shown in FIG. 2, is placed horizontally so that it can be in a vertical direction compared to an air flow that is sucked in through the air suction nozzle 112. As a result, the air sucked in at the air suction nozzle 112 collides with the capturing carrier 102 and then changes its flow to a horizontal direction. At that moment, particles such as air-borne microorganisms and the like are captured by the gel phase polymer due to collision caused by an inertia force.

The capturing device 100, which consists of the capturing carrier 102 and the vessel 103, is supported by the holder 113. Between the outer surface of the holder 113 and the inside wall of the lower member 111b, a gap is formed. Thus, the air flowing in a horizontal direction after colliding with the capturing carrier 102 passes through the gap and flows downward, and then eventually released through the exhaust duct 117.

At the bottom part of the holder 113, the temperature controlling apparatus 114 is installed. This temperature controlling apparatus 114 is controlled to heat the capturing carrier 102 to the temperature of phase transition with high accuracy. In addition, a heating means for the capturing carrier 102 is not limited to a heater, and any apparatus which is capable of heating the capturing carrier 102 to the temperature of phase transition can be used. For example, surrounding the capturing carrier 102 a jacket may be installed to have hot water flow around the carrier, or air which is sucked in through the air section nozzle 112 may be heated.

Air can be absorbed into the capturing apparatus 111 by setting the capturing device 100 under the air suction nozzle 112 and running the pump 116. As a result, the air is sucked in from the air section nozzle 112 in a vertical lower direction, and the air changes its flow in a horizontal direction after collision with the capturing carrier 102 and the air-borne microorganisms can be captured in the gel phase capturing carrier 102.

After the capturing, the capturing carrier 102 is heated to the phase transition temperature of the polymer by the temperature controlling apparatus 114. As a result, having phase transition of the polymer from a gel state to a sol state, the microorganisms which have been captured in the capturing carrier 102 are suspended in the polymer in sol phase, and at the same time, a test reagent which has been kept in the capturing carrier 102 is eluted and added to the microorganisms. Thus, at least one process of adding a test reagent to microorganisms and carrying out a reaction thereof can be performed in the capturing carrier 102, which can save the process required for the subsequent test apparatus.

The microorganisms are recovered in the vessel 103 of the capturing device 110. Because the recovered microorganisms can be set in the subsequent test apparatus (not shown) as they are contained in the vessel 103, the test can be carried out more easily in short time.

Although the present embodiments are related to an example wherein an ATP eliminating agent, a germination inducing factor, an ATP extracting agent, and a luminescent reagent are added, the reagents that can be added are not limited thereto. Rather, some of the reagents can be omitted or other additional reagents can be added if necessary. In addition, although it is not specifically limited to the following, the microorganisms that can be a subject for capturing and testing of the present invention include *Bacillus cereus, Bacillus spizizenii, Corynebacterium renale, Micrococcus luteus, S. aureus, S. epidermidis, Citrobacter freundii, Pseudomonas aeruginosa, Serratia marcescens* and the like.

For the capturing carrier 102 of the fourth embodiment, an ATP eliminating agent and a germination inducing factor are contained as a test reagent in a gel phase polymer. As an ATP eliminating agent, for example, at least one selected from a group consisting of apyrase, alkaline phosphatase, acidic phosphatase, hexokinase, adenosine triphosphatase, and adenosine phosphate deaminase is used. Further, as a germination inducing factor, for example, an amino acid or L-alanine is used. When L-alanine is used as a germination inducing factor, it is preferably used in an amount of 25 mM or more, since if its concentration is too low compared to the polymer, germination inducing activity for a spore-forming bacteria becomes insufficient. On the other hand, if the concentration is too high a gel having sufficient strength cannot be obtained. As such, the concentration is preferably 100 mM or less.

A preferable example of the composition of the capturing carrier 102 described in the above is as follows:

8% (w/v) gelatin (Wako Company (077-03155)),

25% (v/v) Glycerol (Kanto Chemical Corporation (17029-00)),

1% (v/v) ATP eliminating agent (included in Lucifer HS set (60315) which is manufactured by Kikkoman Corp.), 25% (v/v) Phosphate buffer (Phosphate buffer (20012-027) pH 7.2 by Invitrogen Co.), 50 mM L-Alanine (L Alanine (1007-1 M) by Kanto Chemical Corporation), In addition, as to the size of the capturing carrier 102, the one having the diameter of 440 mm and the thickness of 0.8 to 4 mm can be preferably used.

Meanwhile, as to the capturing apparatus 111, the heating means for heating the capturing carrier 102 is controlled so that the capturing carrier 102 can be maintained at the temperature of between 30° C. and 37° C. for 30 minutes or more. When the heating temperature is lower than 30° C., germination may not occur even after heating for long time, and therefore ATP cannot be extracted from the spore-forming microbe. On the other hand, when the heating temperature is higher than 40° C., cell death due to an increased amplification activity under a nutrient deficient environment or inactivation by heat itself can be caused, depending on the subject bacteria.

Figure 11:
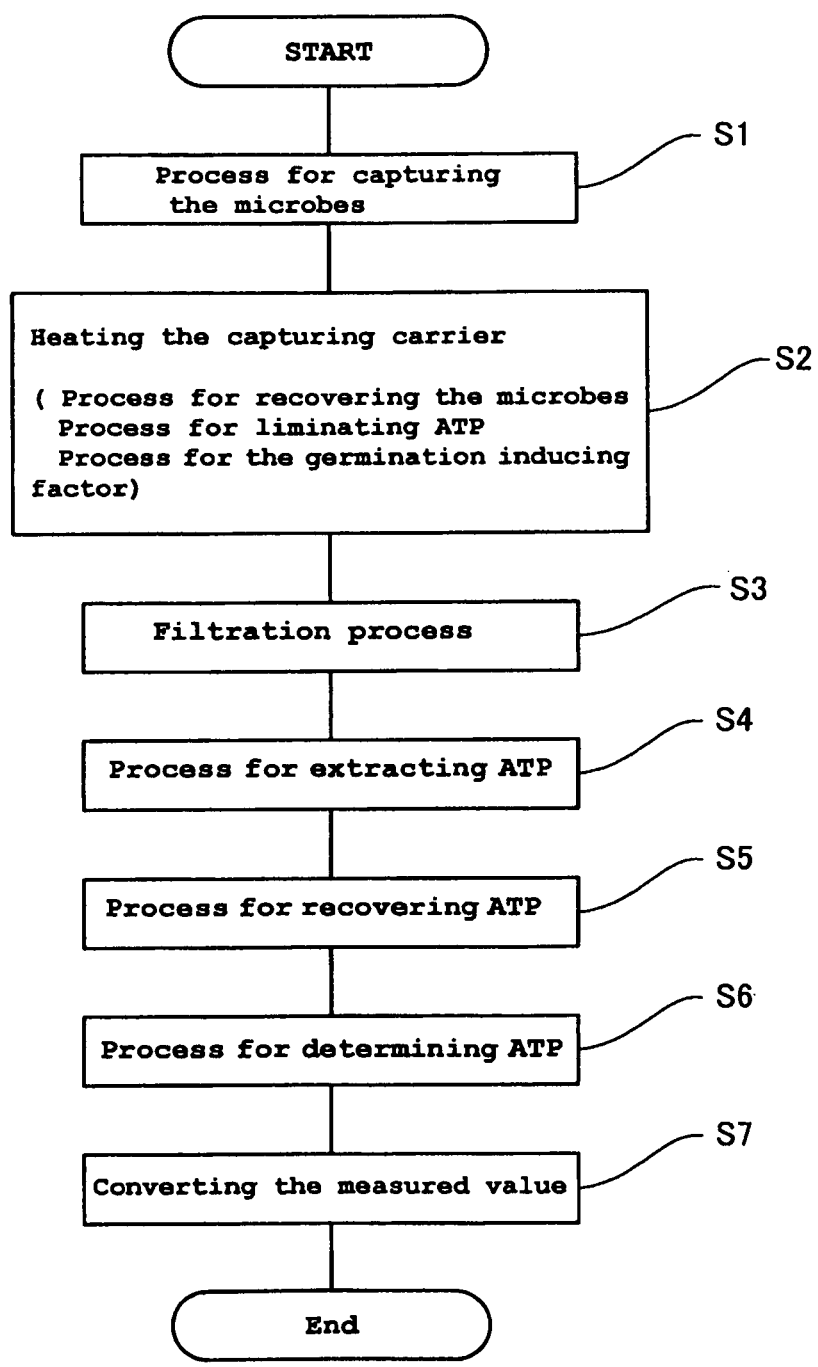
FIG. 11 is a flow chart which shows the procedure of a method for the capturing and the testing according to the fourth embodiment of the present invention.

Next, a method for capturing and testing which is carried out using the capturing apparatus 111 according to the fourth embodiment as described in the above is explained in view of FIG. 11.

First, the capturing device 100 is set and by running the pump 116 (see FIG. 2) air-borne microorganisms are captured in the polymer of the capturing carrier 102 (Step S1). Next, the capturing carrier 102 is heated to the phase transition temperature so that the polymer is subjected to a phase transition from a gel phase to a sol phase (Step S2). As a result, the microorganisms which have been captured in the capturing carrier 102 are suspended in a solated polymer and then recovered, and at the same time an ATP eliminating agent and a germination inducing factor are eluted from the polymer, thus a process of eliminating ATP and a process of inducing germination can be simultaneously carried out. As a result, free ATPs existing outside the body of viable cells are eliminated, followed by a contact of the microorganisms with the germination inducing factor to have a spore-forming microbe sporulate.

Once the process of eliminating ATP and the process of inducing germination are completed, the microorganisms are recovered in the vessel 103 by filtering treatment (Step S3). The vessel 103 is set in a measurement apparatus (not shown), and the ATP extracting agent is added to this measurement apparatus (Step S4). The ATP extracting agent is a reagent which can lyse the cell membrane of viable microbes to extract the ATPs contained inside the cells. For example, a surfactant, trichloroacetic acid (TCA), Tris buffer solution, ethanol, a lytic enzyme having a protease activity and the like are used as the ATP extracting agent. That is, as the cell membrane of the microorganisms is lysed by the ATP extracting agent and the ATPs contained inside the cells are extracted, the measurement of ATP becomes possible. Consequently, a luminescent reagent is added (Step S5) and by aliquoting its reaction solution the luminescence output is measured (Step S6). The measurement of luminescence output is carried out by comparison with the luminescence output of a standard sample, for example, using a luminometer (Berthold Detection Systems, type FB12). The measured luminescence output is converted to the ATP amount, which is then again converted to microbial cell count (Step S7). Thus obtained amount of the microorganisms represents the amount of every viable microbes including spore-forming microbes.

According to the present embodiment, not only the capturing of microorganisms but also the recovery of the captured microorganism and the simultaneous addition of the ATP eliminating agent and the germination inducing factor can be carried out by using the capturing carrier 102, the number of reagents that have to be added to a measurement apparatus can be reduced. As a result, efforts and time required for the measurement can be reduced. In particular for the present embodiment, because the addition of the germination inducing factor, which requires some time for its reaction, can be done before it is placed in the measurement apparatus, time required for the measurement can be drastically reduced.

Furthermore, although a temperature controlling apparatus and a capturing apparatus are comprised in the present embodiment, they can be provided for the measurement apparatus for the next step so that Step S2 and the remaining steps can be carried out within the measurement apparatus.

The Fifth Embodiment

For the capturing carrier 102 of the fifth embodiment, only the ATP eliminating agent is contained in a gel phase polymer. In addition, for a subsequent measurement apparatus, the germination inducing factor, the ATP extracting agent and the luminescent reagent are sequentially added and then the luminescence output is measured. That is, for the flow shown in FIG. 11, "process of the germination inducing" of Step S2 is carried out between Step S2 and Step S3.

According to the fifth embodiment, by heating the capturing carrier 102 the polymer is subjected to a phase transition from a gel phase to a sol phase. As a result, the microorganisms are recovered from the capturing carrier 102 and at the same time the ATP eliminating agent is added thereto. Therefore, efforts and time required for adding the ATP eliminating agent in the measurement apparatus can be saved.

The Sixth Embodiment

For the capturing carrier 102 of the fifth embodiment, only the germination inducing factor is contained in a gel phase polymer. In addition, for a subsequent measurement apparatus, the ATP eliminating agent, the ATP extracting agent and the luminescent reagent are sequentially added and then the luminescence output is measured. That is, for the flow shown in FIG. 11, "process of the ATP eliminating" of Step S2 is carried out between Step S2 and Step S3.

In addition, the ATP eliminating agent is added after adding the germination inducing factor but before completing the reaction of the added germination inducing factor (i.e., typically within 30 minutes).

According to the sixth embodiment, by subjecting a polymer of the capturing carrier 102 to a phase transition from a gel phase to a sol phase, the microorganisms are recovered from the capturing carrier 102 and at the same time the germination inducing factor is added thereto. Therefore, efforts and time required for adding the germination inducing factor in the measurement apparatus can be saved.

The Seventh Embodiment

For the capturing carrier 102 of the seventh embodiment, two kinds of polymers having a different phase transition temperature between a gel and sol are laminated on top of each other. The upper side polymer (i.e., the side for capturing microorganisms) of these two types of polymers has a lower phase transition temperature compared to that of the lower side polymer, and as a result, under heating it undergoes a phase transition to a sol faster than the lower side polymer. In addition, the upper side polymer contains the ATP eliminating agent and the germination inducing factor while the lower side polymer contains the ATP extracting agent.

In addition, as to the capturing apparatus 111 according to the seventh embodiment, the temperature controlling apparatus 114 for heating the capturing carrier 102 is constructed so as to control the temperature in two steps. Specifically, it is constructed to heat the capturing carrier 102 with the phase transition temperature of the upper side polymer and with the phase transition temperature of the lower side polymer.

According to the seventh embodiment, the microorganisms are captured in the upper side polymer of the capturing carrier 102. When these microorganisms are recovered, the capturing carrier 102 is first heated to the phase transition temperature of the upper side polymer. By doing so, while the lower side polymer remains in a gel phase, only the upper side polymer undergoes a phase transition to a sol phase. As a result, at the same time the microorganisms are recovered from the upper side polymer, the ATP eliminating agent and the germination inducing factor are eluted from the upper side polymer. Thus, the free ATPs are eliminated and the microorganisms in a spore state can sporulate. The microorganisms to which the ATP eliminating agent and the germination inducing factor are added are maintained on the lower side polymer.

Next, the capturing carrier 102 is heated to the phase transition temperature of the lower side polymer. By doing so, the lower side polymer undergoes a phase transition to a sol phase and the APT extracting agent is eluted. As a result, the ATP extracting agent is added to the microorganisms, causing the degradation of cell membrane of the microorganisms and the ATPs contained in the microorganisms are extracted.

After a luminescent reagent is added to the ATPs extracted from the microorganisms, the luminescence output is measured.

According to the seventh embodiment, because two kinds of polymers having a different phase transition temperature are laminated and a different kind of reagent is contained in each polymer, multiple reagents can be added in a specific order to the capturing carrier 102 by controlling the heating temperature. As a result, a step of adding reagents in the measurement apparatus can be omitted, thus the efforts and time required therefor can be drastically reduced.

The Eighth Embodiment

For the capturing carrier 102 of the eighth embodiment, three kinds of polymers having a different phase transition temperature between a gel and sol are laminated on top of each other in three layers. The uppermost side polymer (i.e., the side for capturing microorganisms) of these three types of polymers has the lowest phase transition temperature, and as a result, under heating it undergoes a phase transition to a sol faster than the lower side polymers. In addition, the uppermost side polymer contains the ATP eliminating agent, the middle layer polymer contains the germination inducing factor, and the bottom side polymer contains the ATP extracting agent.

In addition, as to the capturing apparatus 111 according to the eighth embodiment, the temperature controlling apparatus 114 for heating the capturing carrier 102 is constructed so as to control the temperature in three steps. Specifically, it is constructed to control the temperature with the phase transition temperature of the uppermost side polymer, with the phase transition temperature of the middle layer polymer, and with the phase transition temperature of the bottom side polymer.

According to the eighth embodiment, the microorganisms are captured in the uppermost side polymer of the capturing carrier 102. When these microorganisms are recovered, the capturing carrier 102 is first heated to the phase transition temperature of the uppermost side polymer. By doing so, while the middle layer and the bottom side polymers remain in a gel phase, only the uppermost side polymer undergoes a phase transition to a sol. As a result, at the same time the microorganisms are taken out of the uppermost side polymer, the ATP eliminating agent is eluted from the uppermost side polymer to eliminate the free ATPs. Then, the microorganisms of which free ATPs are eliminated are maintained on the middle layer polymer.

Next, the capturing carrier 102 is heated to the phase transition temperature of the middle layer polymer. By doing so, the middle layer polymer undergoes a phase transition to a sol while the bottom side polymer is maintained in a gel phase. Thus, the germination inducing factor is eluted from the middle layer polymer and added to the microorganisms, causing the germination of the microorganisms.

Next, the capturing carrier 102 is heated to the phase transition temperature of the bottom side polymer. By doing so, the bottom side polymer undergoes a phase transition to a sol phase while the ATP extracting agent is eluted. As a result, the ATP extracting agent is added to the microorganisms, causing the degradation of cell membrane of the microorganisms and the ATPs contained in the microorganisms are extracted.

After a luminescent reagent is added to the ATPs extracted from the microorganisms, the luminescence output is measured.

According to the eighth embodiment, because three kinds of polymers having a different phase transition temperature are laminated and a different kind of reagent is contained in each polymer, multiple reagents can be added in a specific order to the capturing carrier 102 by controlling the heating temperature. As a result, a step of adding multiple reagents in the measurement apparatus can be omitted, thus the efforts and time required therefor can be drastically reduced.

Furthermore, according to the seventh and the eighth embodiments, the lower (bottom) side polymer can be formed to have a concave shape having a dip in the center and the upper side polymer can be formed over the dip.

Furthermore, although the ATP eliminating agent, the germination inducing factor, and the ATP extracting agent are selectively contained in the capturing carrier 102 according to the fourth to the eighth embodiments described above, other reagents such as the luminescent reagent can be contained in the capturing carrier 102.

Furthermore, although the vessel 103 is housed in the capturing carrier 102 according to the fourth to the eighth embodiments described above, it is not specifically limited thereto and an embodiment having no vessel 103 can be also envisaged. For such case, it can be considered that the capturing carrier 102 is placed on top of a filter, which can filter the sol phase polymer while keeping the microorganisms. As a filter, for example, a membrane filter made of polyvinylidene fluoride with pore diameter of 0.45 μm and the like can be used.

Furthermore, although the above described embodiments are related to an example of capturing and testing air-borne microorganisms, the use of the present invention is not limited thereto and it can be applied to a capturing carrier, a capturing unit, a capturing apparatus and a method for capturing and testing air-borne microorganisms.

Furthermore, although the above described embodiments are related to the use of a polymer which undergoes a phase transition by heating, other polymers that undergo a phase transition by a different factor can be also used. For example, a polymer which undergoes a phase transition from a gel to a sol by a chemical inert to the microorganisms can be used.

Furthermore, for the above described embodiments, the reagents can be comprised inside a microcapsule to get dispersed in the polymer gel.

Furthermore, when multiple polymer layers are laminated as the above seventh and the eighth embodiments, the components of the lower polymer layer can be included in a thermosensitive microcapsule and the resulting microcapsule is dispersed and embedded in the upper polymer layer. Specifically, when the polymer layers are numbered in an order of phase transition and there are n layers, the components of the $(n+1)^{th}$ layer can be comprised in a thermosensitive microcapsule and the resulting microcapsule can be dispersed and embedded in the $n^{th}$ layer. By doing so, contact area and mixing ratio between them can be improved.

Still furthermore, when multiple polymer layers are laminated as the above seventh and the eighth embodiments, magnetic particulates of which surface is immobilized with the components of a polymer layer can be placed in the interface region with the upper polymer layer, followed by subjecting the upper polymer layer to a phase transition to a sol phase and mixing and reacting the particulates by shaking them with an aid of external magnetic field. Specifically, when the polymer layers are numbered in an order of phase transition and there are n layers, the magnetic particulates of which surface is immobilized with the components of the $(n+1)^{th}$ layer can be placed in the interface region with the $n^{th}$ layer, followed by subjecting the $n^{th}$ layer to a phase transition to a sol phase and mixing and reacting the particulates by shaking them with an aid of external magnetic field. In this case, since a control means other than the temperature condition is employed, an accuracy of the control can be improved.

Preferred concentration, reaction temperature and reaction time of a germination inducing factor were obtained by an experiment. For this experiment, to fungus liquid comprising spores of *Bacillus subtilis*, L-alanine was added as a sample in advance. To an aliquot of the resulting mixture, an ATP eliminating agent was added. After 30 minutes, an ATP extracting agent was added and with an aliquot of the resulting mixture a luminescence measurement was carried out.

Figure 12:
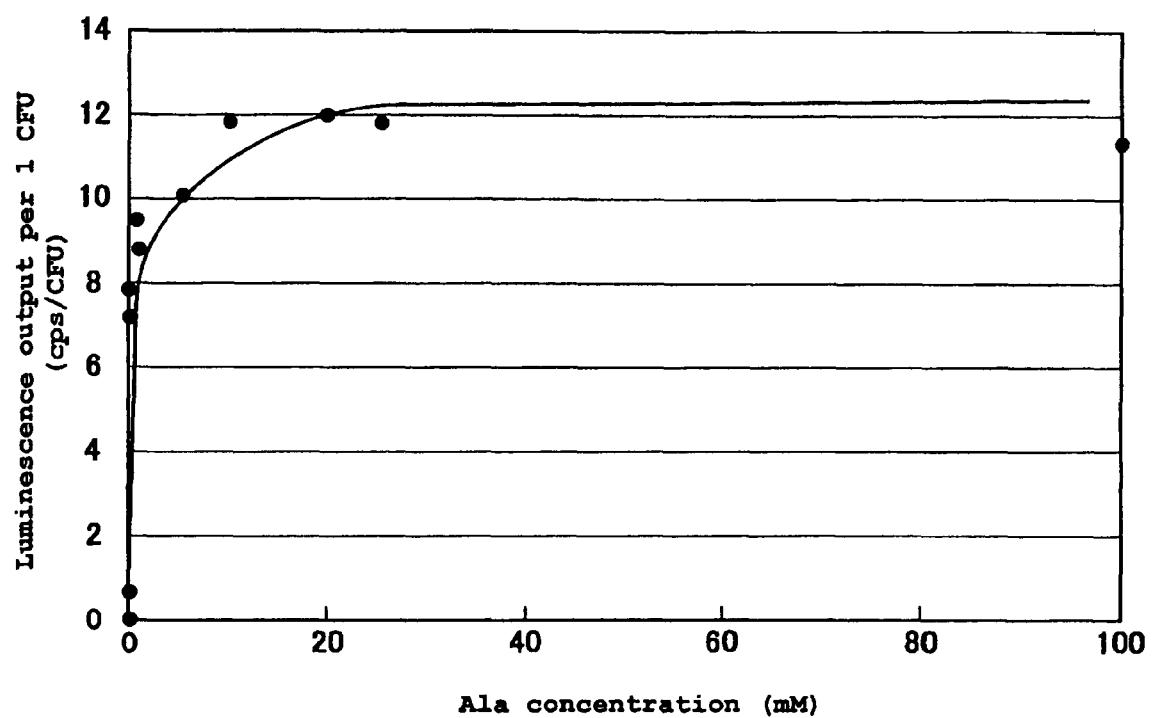
FIG. 12 is a view which shows the relationship between the Ala treatment concentration and the luminescence output.

For this test, concentration of L-alanine (herein after, "Ala concentration") was varied first to obtain the luminescence output. The obtained luminescence output corresponds to a luminescence output per 1 CFU (i.e., one microorganism in a sample before culture). The results are shown in FIG. 12. Further, cps, which is the unit of luminescence output, indicates the number of photoelectrons that are counted during one second.

As it can be seen from FIG. 12, the luminescence output increases with Ala concentration. When Ala concentration was 25 mM or more, the luminescence output was stabilized. That is, when Ala concentration was 25 mM or more, cells can sufficiently sporulate and ATPs can be extracted. As such, it was found that the Ala concentration is preferably 25 mM or more. However, when Ala concentration is too high, a gel with sufficient strength cannot be obtained. For such reasons, Ala concentration is preferably 100 mM or less.

Figure 13:
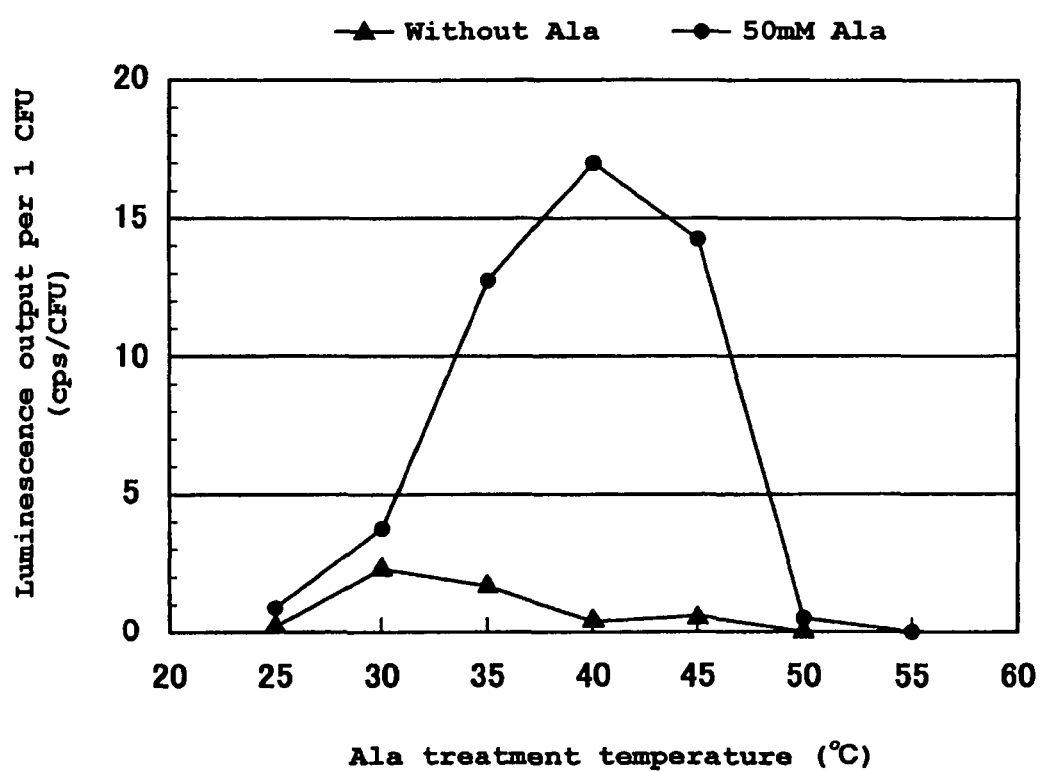
FIG. 13 is a view which shows the relationship between the Ala treatment temperature and the luminescence output.

Next, the relationship between the temperature and the luminescence output for a reaction with L-alanine was investigated. The results are shown in FIG. 13. As it can be seen from FIG. 13, the germination of a spore-forming microbe is facilitated and the luminescence output increases at higher reaction temperature with L-alanine. In particular, at the temperature of 30° C. or higher, the luminescence output dramatically increased. However, after reaching its peak at 40° C., the luminescence output starts to decrease at higher temperatures. Further, although not shown in the figure, when the treatment temperature is more than 40° C. the bacterial cells slowly start to die. As such, it is preferable that the temperature for the reaction with L-alanine is from 30° C. to 40° C. Thus, for eluting the spore-forming microbes by heating the capturing carrier 102, the temperature is preferably between 30° C. and 40° C.

Figure 14:
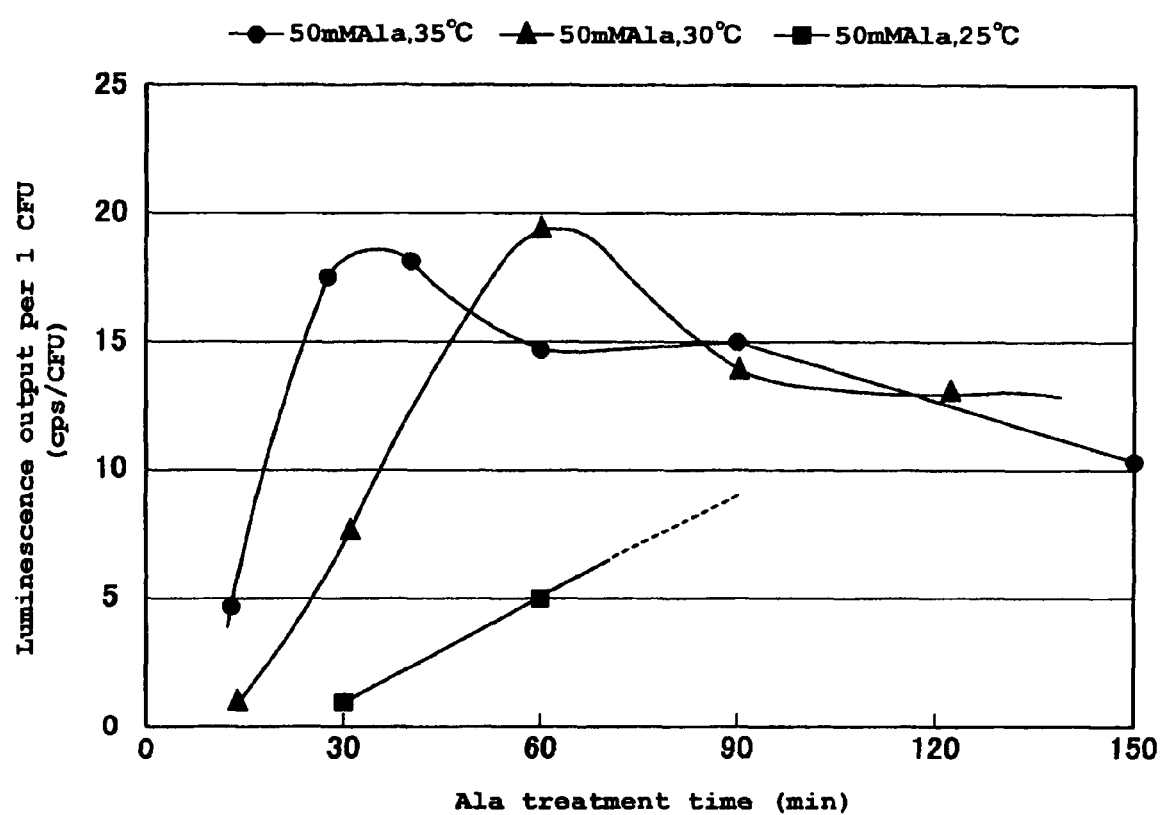
FIG. 14 is a view which shows the relationship between the Ala treatment time and the luminescence output.

Next, for each reaction temperature, change in the luminescence output with time was investigated. The results are shown in FIG. 14. As it can be seen from FIG. 14, when the reaction temperature was 35° C., the highest peak was obtained after 30 minutes. Therefore, when the reaction temperature is 35° C., the reaction time is preferably 30 minutes or more.

As it is clear from the above described description, the present invention may have the specific aspects as follows.

1. A capturing carrier for capturing air-borne microorganisms, characterized in that it comprises a polymer which undergoes a phase transition between a gel and a sol in the temperature range between 15° C. and 40° C.

2. The capturing carrier of the above invention 1, characterized in that the capturing carrier comprises alcohols having no bactericidal activity.

3. The capturing carrier of the above invention 2, characterized in that the alcohols are any one of glycerol, ethylene glycol and propylene glycol.

4. The capturing carrier of the above invention 1, characterized in that the polymer is any one of gelatin or NAGAm/MBPDA.

5. The capturing carrier of the above invention 2, characterized in that the alcohols are glycerol and the glycerol is comprised in an amount of 30% to 60% by weight compared to the capturing carrier.

6. The capturing carrier of the above invention 1, characterized in that the polymer is gelatin and the gelatin is comprised in an amount of 5% to 10% by weight compared to the capturing carrier.

7. The capturing carrier of the above invention 1, characterized in that the polymer is NAGAm/MBPDA and the NAGAm/MBPDA is comprised in an amount of 1% to 10% by weight compared to the capturing carrier.

8. The capturing carrier of the above invention 1, characterized in that the capturing carrier consists of a polymer which is in a gel phase at the time of capturing microorganisms but undergoes a phase transition to a sol phase at the temperature of 40° C. or less under heating, and by containing a test reagent in the polymer the test reagent is eluted upon the phase transition from a gel phase to a sol phase. According to the present invention, since the polymer consisting of the capturing carrier is in a gel phase at the time of capturing microorganisms, the air-borne microorganisms can be captured efficiently. Further, since the carrier undergoes a phase transition to a sol phase at the temperature of 40° C. or less under heating, the microorganisms which have been captured in the capturing carrier can be easily recovered from the carrier, without being destroyed. Still further, according to the present invention, since the test reagent is contained in the gel phase polymer and eluted upon a phase transition to a sol phase, the test reagent can be added to the microorganisms at the same time they are taken out from the capturing carrier. As such, according to the present invention, the processes of recovering the microorganisms from the capturing carrier, and adding the test reagent thereto can be carried out simultaneously. In summary, by using the capturing carrier of the present invention, the processes of capturing the air-borne microorganisms, taking out the microorganisms from the carrier, and adding the test reagent thereto can be done so that processes from capturing to testing of the air-borne microorganisms can be done conveniently in short time.

9. With respect to the invention of the above invention 8, the test reagent is characterized in that it is a reagent for detecting the captured microorganisms by ATP method. Thus, when a number of reagents are required like the ATP method, with an application of the present invention efforts and time required for the process from capturing to testing of the microorganisms can be dramatically reduced.

10. With respect to the invention of the above invention 9, the reagent is characterized in that it is an ATP eliminating agent which eliminates ATP other than the ATP originating from the microorganisms. According to the present invention, when the microorganisms are recovered in accordance with a phase transition of the capturing carrier from a gel to a sol, the ATP eliminating agent is eluted and added thereto. As such, free ATPs existing outside the cell body of viable microbes can be removed. Thus, according to the corresponding invention 10, the processes of recovering the microorganisms from the capturing carrier, and removing the free ATPs can be carried out simultaneously.

11. With respect to the invention of the above invention 10, the ATP eliminating agent is characterized in that it comprises at least one selected from a group consisting of apyrase, alkaline phosphatase, acidic phosphatase, hexokinase, adenosine triphosphatase, and adenosine phosphate deaminase.

12. With respect to the invention of the above invention 9, the test reagent is characterized in that it comprises an ATP extracting agent which can extract the ATP originating from the microorganisms. According to the present invention, when the microorganisms are recovered in accordance with a phase transition of the capturing carrier from a gel to a sol, the ATP eliminating agent is eluted and added thereto. As such, cell membrane of the viable microbes can be lysed. Thus, according to the invention of claim 12, the processes of recovering the microorganisms from the capturing carrier, and performing the lysis of cell membrane of the viable microbes can be carried out simultaneously.

13. With respect to the invention of the above invention 12, the ATP extracting agent is characterized in that it comprises a surfactant, trichloroacetic acid (TCA), tris buffer, ethanol, a lytic enzyme having a protease activity and the like.

14. With respect to the invention of the above invention 9, the reagent is characterized in that it is a germination inducing factor which induces germination of a spore-forming microbe or spores of a plant. According to the present invention, when the microorganisms are recovered in accordance with a phase transition of the capturing carrier from a gel to a sol, the germination inducing factor is eluted and added thereto. As such, by inducing germination of a spore-forming microbe or spores of a plant, cells can be transformed into a general state for which all the reactions of the ATP method can easily occur. Thus, according to the invention 14, the processes of recovering the microorganisms from the capturing carrier, and inducing the germination of cell membrane of a spore-forming microbe or spores of a plant cell can be carried out simultaneously.

15. With respect to the invention of the above invention 14, the germination inducing factor is characterized in that it is either an amino acid or L-alanine.

16. With respect to the invention of the above invention 14, the germination inducing factor is characterized in that it is either sugar or glucose.

17. With respect to the invention of the above invention 8, the capturing carrier is characterized in that it is constructed by lamination of multiple polymers which have a property of undergoing a phase transition from a gel phase to a sol phase and have a different phase transition temperature. According to the present invention, since the capturing carrier is constructed by lamination of multiple polymers which have a different phase transition temperature, by controlling the heating temperature, a polymer which under goes a phase transition from a gel to a sol can be selected. Thus, by changing the test reagent for each type of the polymers, the test reagent for addition can be also selected.

18. With respect to the invention of the above invention 17, the multiple polymers are characterized in that they consist of three layers and the polymer located on the microorganism capturing side has lower phase transition temperature and from the microorganism capturing side an ATP eliminating agent, a germination inducing factor, and an ATP extracting agent are comprised in the order. According to the present invention, when the heating temperature for the capturing carrier is increased, from the side to which the microorganisms are captured the polymer undergoes a phase transition from a gel to a sol. As a result, at the same time the captured microorganisms are taken out from the capturing carrier, the ATP eliminating agent, the germination inducing factor, and the ATP extracting agent are eluted in order and added to the microorganisms. Thus, the processes of recovering the microorganisms from the capturing carrier, eliminating the free ATP, inducing the germination of a spore-forming microbe and the like, and extracting the ATP of the microorganisms can be carried out by a single capturing carrier, resulting in a dramatic increase in the efficiency for the processes from capturing to testing.

19. With respect to the invention of the above invention 17, the multiple polymers are characterized in that they consist of two layers and the polymer located on the microorganism capturing side has lower phase transition temperature compared to the polymer on the other side and in the polymer located on the microorganism capturing side an ATP eliminating agent and a germination inducing factor are comprised while in the polymer on the other side an ATP extracting agent is comprised. According to the present invention, when the heating temperature for the capturing carrier is increased, starting from the side to which the microorganisms are captured the polymer undergoes a phase transition from a gel to a sol. As such, at the same time the captured microorganisms are taken out from the capturing carrier, the ATP eliminating agent and the germination inducing factor are eluted and added to the microorganisms followed by the elution and addition of the ATP extracting agent. Thus, according to the present invention, all the processes of recovering the microorganisms from the capturing carrier, eliminating the free ATP, inducing the germination of a spore-forming microbe and the like, and extracting the ATP of the microorganisms can be carried out by a single capturing carrier, resulting in a dramatic increase in the efficiency for the processes from capturing to testing.

20. A capturing device for capturing air-borne microorganisms, characterized in that it comprises a capturing carrier comprising a polymer which undergoes a phase transition between a gel and a sol in the temperature range between 15° C. and 40° C., and a vessel to contain the capturing carrier.

21. The capturing device of the above invention 20, characterized in that a filter is comprised at the bottom of the vessel.

22. The analysis system is characterized in that it comprises a holding member which holds the capturing carrier comprising a polymer which undergoes a phase transition between a gel and a sol in the temperature range between 15° C. and 40° C., a temperature controlling apparatus which controls the temperature of the capturing carrier, and an air stream controlling part which introduces air flow to the capturing carrier.

23. The analysis system of the above invention 22, characterized in that the temperature controlling apparatus can switch the heating and the cooling of the capturing carrier before and after the introduction of air flow to the capturing carrier.

24. The analysis system of the above invention 22, characterized in that, for the capturing carrier, the gel phase polymer is placed on the filter for filtering a sol, a grid plate holding part which holds a grid plate constituting a filtration apparatus in combination with the filter is comprised, and the filtration apparatus can filter the polymer that is transformed into a sol by the temperature controlling apparatus.

25. The method for capturing and testing air-borne microorganisms of the present invention is characterized in that it comprises steps of capturing microorganisms by which the air-borne microorganisms are captured in a capturing carrier by spraying air comprising air-borne microorganisms to the capturing carrier which consists of a polymer in gel phase and contains a test reagent, and recovering and adding by which the capturing carrier is heated at the temperature of 40° C. or less for a phase transition to a sol phase so that the microorganisms captured in the capturing carrier are recovered from the capturing carrier and at the same time the test reagent is eluted from the capturing carrier, which has undergone a phase transition to a sol phase, and then added to the microorganisms above. According to the present invention, the processes of recovering the microorganisms from the capturing carrier and the process of adding the test reagent to them can be carried out simultaneously, resulting in simplification of the operational process and shortening of the operation time.

What is claimed is:

1. A capturing carrier for capturing air-borne microorganisms comprising:
    a polymer that undergoes a phase transition from a gel to a sol in the temperature between 15° C. and 40° C.; and
    an ATP eliminating agent mixed in the polymer that eliminates ATP other than ATP originating from the microorganisms, wherein the ATP eliminating agent can be eluted with the polymer when said phase transition from the gel phase to the sol phase occurs.

2. The capturing carrier according to claim 1, wherein the polymer is one of a gelatin and a copolymer of N-acryloylglycineamide and N-methacroyl-N'-biotinylpropylenediamine (NAGAm/MBPDA).

3. The capturing carrier according to claim 1, comprising a glycerol in an amount of 30% to 60% by weight compared to the capturing carrier.

4. The capturing carrier according to claim 1, wherein the polymer is a gelatin present in an amount of 5% to 10% by weight compared to the capturing carrier.

5. The capturing carrier according to claim 1, wherein the polymer is NAGAm/MBPDA present in an amount of 1% to 10% by weight compared to the capturing carrier.

6. The capturing carrier according to claim 1, wherein
    the polymer is in a gel phase at or near room temperature and undergoes a phase transition to a sol phase when heated to a temperature between 25° C. and 37° C., and
    the ATP eliminating agent is combined with the polymer so that the ATP eliminating agent can be eluted with the polymer when said phase transition from the gel phase to the sol phase occurs.

7. The capturing carrier according to claim 1, further comprising a reagent for detecting the captured microorganisms by ATP method.

8. The capturing carrier according to claim 7, wherein the reagent comprises an ATP extracting agent which can extract ATP originating from the microorganisms.

9. The capturing carrier according to claim 8, wherein the ATP extracting agent comprises at least one member selected from the group consisting of a surfactant, trichloroacetic acid (TCA), tris buffer, ethanol, and a lysozyme having a protease activity.

10. The capturing carrier according to claim 1, wherein the ATP eliminating agent comprises at least one member selected from the group consisting of apyrase, alkaline phosphatase, acidic phosphatase, hexokinase, adenosine triphosphatase, and adenosine phosphate deaminase.

11. The capturing carrier according to claim 1, further comprising a germination inducing factor that induces germination of spore-forming microbes or spores of a plant.

12. The capturing carrier according to claim 11, wherein the germination inducing factor is an amino acid.

13. The capturing carrier according to claim 11, wherein the germination inducing factor is either sugar or glucose.

14. The capturing carrier according to claim 1, wherein the capturing carrier is constructed by lamination of multiple polymers which have a property of undergoing a phase transition from a gel phase to a sol phase and have different phase transition temperatures from one another.

15. The capturing carrier according to claim 14, wherein
    the multiple polymers consist of three layers,
    a polymer in the layer closer to a microorganism capturing side has lower transition temperature than the other layers, and
    from the microorganism capturing side, the first layer comprises an ATP eliminating agent, the second layer comprises a germination inducing factor, and the third layer comprises an ATP extracting agent.

16. The capturing carrier according to claim 14, wherein
    the multiple polymers consist of two layers,
    the polymer located on a microorganism capturing side has lower transition temperature compared to the polymer on the other side,
    in the polymer located on the microorganism capturing side, an ATP eliminating agent and a germination inducing factor are present, and
    in the polymer on the other side, an ATP extracting agent is present.

17. The capturing carrier of claim 1, further comprising alcohols having no bactericidal activity.

18. The capturing carrier of claim 17, wherein the alcohols are selected from the group consisting of glycerol, ethylene glycol, and propylene glycol.

19. The capturing carrier of claim 1, wherein the polymer is a gel at room temperature.

20. A capturing device for capturing air-borne microorganisms comprising:
    a capturing carrier comprising a polymer that undergoes a phase transition from a gel to a sol in the temperature range between 15° C. and 40° C.;
    an ATP eliminating agent mixed in the polymer that eliminates ATP other than ATP originating from the microorganisms, wherein the ATP eliminating agent can be eluted with the polymer when said phase transition from the gel phase to the sol phase occurs; and
    a vessel, having a filter at a bottom of the vessel, to contain the capturing carrier.

21. The capturing device of claim 20, wherein the filter is configured to filter the polymer when it is in the sol phase and to collect microbes.

22. An analysis system comprising:
    a holding member that holds a capturing carrier comprising a polymer that undergoes a phase transition from a gel to a sol in the temperature range between 15° C. and 40° C.;
    an ATP eliminating agent mixed in the polymer that eliminates ATP other than ATP originating from the microorganisms, wherein the ATP eliminating agent can be eluted with the polymer when said phase transition from the gel phase to the sol phase occurs;
    a temperature controlling apparatus that controls the temperature of the capturing carrier; and
    an air stream controlling part that introduces air flow to the capturing carrier, wherein
    the capturing carrier comprises a gel phase polymer on top of a filter for filtering a sol after the phase transition from the gel to the sol, a grid plate holding part holds a grid plate that constitutes a filtration apparatus when combined with the filter, and the filtration apparatus filters the polymer that is transformed into a sol by the temperature controlling apparatus.

23. The analysis system according to claim 22, wherein the temperature controlling apparatus can switch the heating and the cooling of the capturing carrier before and after the introduction of air flow to the capturing carrier.

24. The analysis system of claim 22, wherein the filter is configured to filter the polymer when it is in the sol phase and to collect microbes.

25. A method for capturing and testing air-borne microorganisms comprising:
   capturing air-borne microorganisms in a capturing carrier by spraying air comprising the air-borne microorganisms to the capturing carrier that consists of a polymer in gel phase and contains an ATP eliminating agent; and
   recovering and adding where the capturing carrier is heated at 40° C. or less to initiate a phase transition of the gel phase polymer to a sol phase so that the air-borne microorganisms captured in the capturing carrier are recovered from the capturing carrier and at the same time the ATP eliminating agent is eluted from the capturing carrier, which has undergone the phase transition to the sol phase, and then added to the microorganisms above.

* * * * *